US006225065B1

(12) United States Patent
Kitabayashi et al.

(10) Patent No.: US 6,225,065 B1
(45) Date of Patent: May 1, 2001

(54) KIT FOR AMPLIFYING NUCLEIC ACID

(75) Inventors: Masao Kitabayashi; Taku Arakawa; Hiroaki Inoue; Bunsei Kawakami; Yoshihisa Kawamura, all of Tsuruga; Tadayuki Imanaka; Masahiro Takagi, both of Suita; Masaaki Morikawa, Minoo, all of (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/418,027

(22) Filed: Oct. 14, 1999

Related U.S. Application Data

(62) Division of application No. 09/073,354, filed on May 6, 1998, now Pat. No. 6,033,859, which is a division of application No. 08/656,005, filed on May 24, 1996, now Pat. No. 6,054,301.

(30) Foreign Application Priority Data

May 31, 1995 (JP) .................................................. 7-134096

(51) Int. Cl.$^7$ ............................. C12Q 1/68; C12P 19/34; C12N 9/00; C07K 1/00; B65D 69/00

(52) U.S. Cl. ........................... 435/6; 435/91.1; 435/91.2; 435/183; 530/350; 206/568

(58) Field of Search ................................ 435/91.2, 91.1, 435/6, 183; 206/568; 530/350

*Primary Examiner*—Eggerton A. Campbell
*Assistant Examiner*—Joyce Tung
(74) *Attorney, Agent, or Firm*—Kenyon & Kenyon

(57) ABSTRACT

A nucleic acid amplifying enzyme having a short reaction time and high fidelity is provided. The enzyme of this invention is a thermostable DNA polymerase having a nucleic acid extension rate of at least 30 bases per second and a 3'–5' exonuclease activity. Also provided are a method and kit for amplifying nucleic acid.

6 Claims, 7 Drawing Sheets

KOD Polymerase (Derived from hyperthermophilic archaeon strain KOD1)
1: Reaction time: 0.3 min
2: Reaction time: 0.7 min
3: Reaction time: 1.0 min
4: Reaction time: 1.3 min
5: Reaction time: 1.7 min KOD Polymerase (Derived from hyperthermophilic archaeon strain KOD1)

1: Reaction time: 0.3 min
2: Reaction time: 0.7 min
3: Reaction time: 1.0 min
4: Reaction time: 1.3 min
5: Reaction time: 1.7 min KOD Polymerase
1: Reaction Time: 0.7 min
2: " " : 1.0 min
3: " " : 1.3 min
4: " " : 1.7 min Pfu Polymerase
1: Reaction Time: 1.0 min
2: " " : 1.5 min
3: " " : 2.0 min
4: " " : 2.5 min Deep Vent Polymerase
1: Reaction Time: 1.5 min
2: " " : 2.0 min
3: " " : 2.5 min Taq Polymerase
1: Reaction Time: 1.0 min
2: " " : 1.5 min
3: " " : 2.0 min
4: " " : 2.5 min

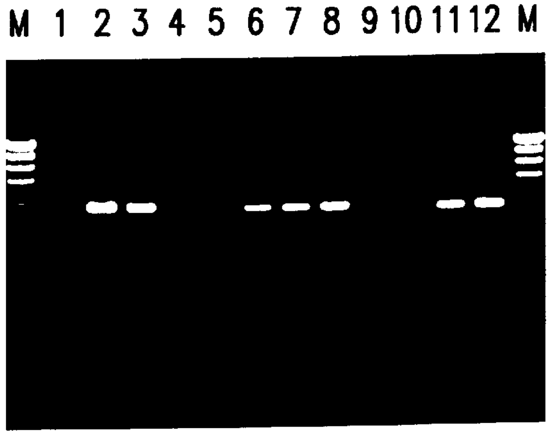

1: KOD Polymerase (Derived from Hyperthermophilic archaeon strain KOD1) Reaction Time: 1 sec.
2: KOD Polymerase (Derived from Hyperthermophilic archaeon strain KOD1) " " : 5 sec.
3: KOD Polymerase (Derived from Hyperthermophilic archaeon strain KOD1) " " :10 sec.
4: Taq Polymerase (Derived from Thermus aquaticus) Reaction Time: 1 sec.
5: Taq Polymerase (Derived from Thermus aquaticus) " " : 5 sec.
6: Taq Polymerase (Derived from Thermus aquaticus) " " : 10 sec.
7: Taq Polymerase (Derived from Thermus aquaticus) " " : 30 sec.
8: Taq Polymerase (Derived from Thermus aquaticus) " " : 60 sec.
9: Pfu Polymerase (Derived from Pyrococcus furiosus) " " : 30 sec.
10: Pfu Polymerase (Derived from Pyrococcus furiosus) " " : 60 sec.
11: Pfu Polymerase (Derived from Pyrococcus furiosus) " " : 90 sec.
12: Pfu Polymerase (Derived from Pyrococcus furiosus) " " :120 sec.

FIG.3

1: pET-8c Precipitate
2: pET-pol (ΔIVS-A, ΔIVS-B) Precipitate
3: pET-8c Supernatant Liquid
4: pET-8c Supernatant Liquid x 5
5: pET-pol (ΔIVS-A, ΔIVS-B) Supernatant Liquid
6: pET-pol (ΔIVS-A, ΔIVS-B) Supernatant Liquid x 5

1: Vent Polymerase (Derived from Thermococcus litoralis)
2: pET-pol (ΔIVS-A, IVS-B) Supernatant Liquid
3: pET-pol (ΔIVS-A, IVS-B) Supernatant Liquid x 5
4: pET-8c Supernatant Liquid
5: pET-8c Supernatant Liquid x 5

KIT FOR AMPLIFYING NUCLEIC ACID

CROSS REFERENCE TO RELATED APPLICATIONS

The present application is a divisional of application Ser. No. 09/073,354 filed May 6, 1998, now U.S. Pat. No. 6,033,859, which is a divisional of application Ser. No. 08/656,005 filed May 24, 1996, now U.S. Pat. No. 6,054,301 the subject matter of which is incorporated herein by reference.

The present invention relates to a method of amplifying nucleic acid wherein DNA or RNA is amplified within a short reaction time and with a high fidelity, to a method of identifying nucleic acid utilizing said amplifying method and to a DNA polymerase and a reagent kit used for those methods.

PRIOR ART

Many studies have been made already for DNA polymerase of mesophilic microorganism such as *Escherichia coli* and for DNA polymerase derived from phages infectable by the mesophilic microorganisms. In addition, many studies have been also made already for heat stable DNA polymerases which are useful in a recombinant DNA technique by means of nucleic acid amplification such as a polymerase chain reaction (PCR). Examples of the heatstable polymerases which are used for the PCR are DNA polymerase ($T^{th}$ polymerase) mostly derived from *Thermus thermophilus* and DNA polymerase (Taq polymerase) derived from *Thermus aquaticus*. Other known examples are DNA polymerase (Pfu polymerase) derived from *Pyrococcus furiosus* and DNA polymerase (Vent polymerase) derived from *Thermococcus litoralis*.

PROBLEMS TO BE SOLVED BY THE INVENTION

However, with the Taq polymerase, fidelity and thermostability upon the synthesis of DNA are not sufficient. Although the Pfu polymerase exhibiting excellent fidelity and thermostability has been developed, said Pfu polymerase has some problems that its DNA extension rate is slow and a processivity is low whereby it has been used only for a specific PCR.

Recently, a PCR whereby 20 kb or more DNA is amplified (hereinafter, referred to as a long-PCR) has been developed. In said long-PCR, both Taq polymerase and Pfu polymerase are mixed whereby properties of both enzymes are utilized. However, when two enzymes having different properties are used in the same reaction system, some discrepancies might occur in their appropriate reaction conditions whereby there is a question whether the high extension rate and fidelity which are the advantages of each of those enzymes can be still maintained. Moreover, because of the difference in the thermostabilities and in the composition of the stock solutions of both enzymes, there is a question as to the stability when they are stored in the same container.

In view of the above, there has been a keen demand for novel thermostable polymerase which exhibits both of those advantages.

MEANS TO SOLVE THE PROBLEMS

The present inventors have succeeded in preparing a thermostable DNA polymerase from a hyperthermophilic archaeon strain KOD1, and, when its properties are investigated, it has been found that said DNA polymerase exhibits the advantages of the above-mentioned two enzymes, i.e. high extension rate and high fidelity, whereby the present invention has been achieved.

Thus, the present invention relates to a method for amplifying a target nucleic acid comprises reacting the target nucleic acid with four kinds of dNTP and primer complementary to said target nucleic acid in a buffer solution which contains a thermostable DNA polymerase having a DNA extension rate of at least 30 bases/second and a 3'–5' activity such that the above mentioned primer is annealed to the target nucleic acid and an extention product is synthesized from the primer.

The present invention further relates to a method for amplifying a target nucleic acid in a sample wherein each target nucleic acid consists of two separate complementary strands which comprises the following steps A to D, characterized in that a thermostable DNA polymerase having a DNA extension rate of at least 30 bases/second and a 3'–5' exonuclease activity is used as a thermostable DNA polymerase;

A: modifying the target nucleic acid, if necessary, to produce single-stranded nucleic acids;

B: reacting the single-stranded nucleic acids with four kinds of dNTP and primers, wherein said primers are selected so as to be sufficiently complementary to different strands of target nucleic acid to anneal therewith, in a buffer solution which contains a thermostable DNA polymerase such that the above mentioned primers are annealed to the single-stranded nucleic acids and extention products are synthesized from the primers, C: separating the primer extention products from the templates on which they are synthesized to produce single-stranded nucleic acids; and D: repeatedly conducting the above mentioned steps B and C.

The present invention further relates to a method for detecting a target nucleic acid in a sample wherein each target nucleic acid consists of two separate complementary strands which comprises the following steps A to E, characterized in that a thermostable DNA polymerase having a DNA extension rate of at least 30 bases/second and a 3'–5' exonuclease activity is used as a thermostable DNA polymerase;

A: modifying the target nucleic acid, if necessary, to produce single-stranded nucleic acids;

B: reacting the single-stranded nucleic acids with four kinds of dNTP and primers, wherein said primers are selected so as to be sufficiently complementary to different strands of target nucleic acid to anneal therewith, in a buffer solution which contains a thermostable DNA polymerase such that the above mentioned primers are annealed to the single-stranded nucleic acids and extention products are synthesized from the primers, C: separating the primer extention products from the templates on which they are synthesized to produce single-stranded nucleic acids;

D: repeatedly conducting the above mentioned steps B and C, and

E: detecting an amplified nucleic acid.

The present invention further relates to a reagent kit for amplifying target nucleic acid which comprises primers, wherein said primers are selected so as to be sufficiently complementary to different strands of target nucleic acid to anneal therewith, four kinds of dNTP, divalent cation, thermostable DNA polymerase having a DNA extension rate of at least 30 bases/second and a 3'–5' exonuclease activity and buffer solution.

The present invention further relates to a reagent kit for detecting target nucleic acid which comprises primers, wherein said primers are selected so as to be sufficiently complementary to different strands of target nucleic acid to anneal therewith, four kinds of dNTP, divalent cation, thermostable DNA polymerase having a DNA extension rate of at least 30 bases/second and a 3'–5' exonuclease activity, amplifying buffer solution, a probe capable of hybridizing with amplified nucleic acid and a detection buffer solution.

The present invention relates to a thermostable DNA polymerase which is obtainable from a strain KOD1 which belongs to a hyperthermophilic archaeon strain.

The present invention relates to an isolated DNA comprising a nucleotide sequence that encodes the thermostable DNA polymerase derived from a KOD1 strain which belongs to hyperthermophilic archaeon The present invention further relates to a recombinant DNA expression vector that comprises the DNA sequence inserted into a vector, wherein the DNA sequence encodes the thermostable DNA polymerase derived from a KOD1 strain which belongs to hyperthermophilic archaeon.

The present invention further relates to a transformed recombinant host cell using a recombinant DNA expression vector that comprises the DNA sequence inserted into a vector, wherein the DNA sequence encodes the thermostable DNA polymerase derived from a KOD1 strain which belongs to hyperthermophilic archaeon.

The present invention relates to a method for producing a DNA polymerase obtainable from a KOD1 strain which belongs to hyperthermophilic archaeon, comprises culturing recombinant host cells which is transformed by a recombinant DNA expression vector that comprises the DNA sequence inserted into a vector, wherein the DNA sequence encodes the thermostable DNA polymerase derived from a KOD1 strain which belongs to hyperthermophilic archaeon, and recovering the produced thermostable DNA polymerase.

The present invention further relates to a method for purifying the DNA polymerase obtainable from a KOD1 strain which belongs to hyperthermophilic archaeon, comprises culturing the recombinant host cells which is transformed by a recombinant DNA expression vector that comprises the DNA sequence inserted into a vector, wherein the DNA sequence encodes the thermostable DNA polymerase derived from a KOD1 strain which belongs to hyperthermophilic archaeon, and further (a) recovering the cultured recombinant host cells, disintegrating them and preparing the cell extract, and (b) removing the impurified proteins derived from recombinant host cells.

The nucleic acid which is to be amplified by the present invention is DNA or RNA. There is no restriction at all for the sample in which such a nucleic acid is contained.

The thermostable enzyme which is used in the present invention is a thermostable DNA polymerase having at least 30 bases/second of DNA extension rate and having a 3'–5' exonuclease activity. Its specific example is a DNA polymerase derived from a hyperthermophilic archaeon strain KOD1 (called a KOD polymerase) and said enzyme may be either a thermostable enzyme purified from nature or an enzyme manufactured by a gene recombination technique.

The DNA extension rate in the present invention is calculated from the relationship between the reaction time and the size of the synthesized DNA in the reaction of various kinds of DNA polymerases such as KOD, Pfu, Deep Vent, Taq, etc. (5U) in each buffer using a substrate prepared by annealing a single-stranded DNA (1.6 μg) of M13 with a primer (16 pmoles) complementary thereto. It is essential in the present invention that the DNA extension rate is at least 30 bases/second.

The DNA extension rates for each of the polymerases are 105–130 bases/second for KOD polymerase, 24.8 bases/second for Pfu polymerase, 23.3 bases/second for Deep Vent polymerase and 61.0 bases/second for Taq polymerase.

On the other hand, it is essential in the present invention that the thermostable DNA polymerase has a 3'–5' exonuclease activity.

In the present invention, the 3'–5' exonuclease activity is determined by checking the rate of release of $^3H$ under the optimum condition for each polymerase using a substrate wherein the 3'-of the lambda-DNA digested with HindIII labeled with [$^3H$]TTP.

In the 3'–5' exonuclease activity of each polymerase, free-$^3H$ is found to be only 10–20% in the case of Taq polymerase and Tth polymerase after an incubation period of three hours, in KOD polymerase and Pfu polymerase, it is 50–70%.

It has been confirmed that the KOD polymerase used in the present invention has a 3'–5' exonuclease activity and that, in the gene which codes for KOD polymerase, there is a DNA conserved sequence showing a 3'–5' exonuclease activity the same as in the case of Pfu polymerase.

In the present invention, the fact whether there is a 3'–5' exonuclease activity is checked in such a manner that KOD polymerase is allowed to stand, using a DNA fragment into which the DNA of [$^3H$]TTP-labelled-lambda-DNA digested with HindIII is incorporated as a substrate, at the reaction temperature of 75° C. in a buffer (20 mM Tris-HCl of pH 6.5, 10 mM KCl, 6 mM $(NH_4)_2SO_4$, 2 mM $MgCl_2$, 0.1% Triton X-100 and 10 μg/ml BSA) and the ratio of the free-[$^3H$]TTP is determined.

At the same time, Taq polymerase and Tth polymerase having no 3'–5' exonuclease activity and Pfu polymerase having a 3'–5' exonuclease activity were checked using a buffer for each of them by the same manner as in the control experiments. The titer of each of the used polymerases was made 2.5 units.

The substrate DNA was prepared in such a manner that, first, 0.2 mM of dATP, dGTP, dCTP and [$^3H$]TTP were added to 10 μg of lambda-DNA digested with HindIII, the 3'-end was elongated by Klenow polymerase, then DNA fragments were recovered by extracting with phenol and precipitating with ethanol and free mononucleotides were removed by a Spin column (manufactured by Clontech).

In the case of KOD polymerase and Pfu polymerase, 50–70% of free [$^3H$]TTP were detected after an incubation period of three hours, in the case of Taq polymerase and Tth polymerase, only 10–20% of free [$^3H$]TTP was noted.

It is preferred that said thermostable DNA polymerase contains an amino acid sequence given in SEQ ID No.1.

It is also preferred that said thermostable DNA polymerase is an enzyme having the following physical and chemical properties.

Action: It has a DNA synthetic activity and a 3'–5' exonuclease activity.

DNA extension rate: at least 30 bases/second

Optimum pH: 6.5–7.5 (at 75° C.)

Optimum temperature: 75° C.

Molecular weight: about 88–90 Kda

Amino acid sequence: as mentioned in SEQ ID No.1

An example of the methods for manufacturing DNA polymerase derived from a hyperthermophilic archaeon strain KOD1 is that thermostable DNA polymerase gene was cloned from strain KOD1 which was isolated from a solfatara at a wharf on Kodakara Island, Kagoshima so that a recombinant expression vector was constructed, then a transformant prepared by transformation by said recombinant vector was cultured and the thermostable DNA polymerase was collected from the culture followed by purifying.

In the present invention, the DNA polymerase derived from the above-mentioned hyperthermophilic archaeon strain KOD1 has a DNA synthesizing activity and a 3'–5' exonuclease activity and has a DNA extension rate of at least 30 bases/second. This property is used for conducting an amplification of nucleic acid.

The amplifying method of the present invention includes the following steps A to D.

A: modifying the target nucleic acid, if necessary, to produce single-stranded nucleic acids;

B: reacting the single-stranded nucleic acids with four kinds of dNTP and primers, wherein said primers are selected so as to be sufficiently complementary to different strands of target nucleic acid to anneal therewith, in a buffer solution which contains a thermostable DNA polymerase such that the above mentioned primers are annealed to the single-stranded nucleic acids and extention products are synthesized from the primers, C: separating the primer extention products from the templates on which they are synthesized to produce single-stranded nucleic acids; and D: repeatedly conducting the above mentioned steps B and C.

In the step A, the target nucleic acid is denatured if necessary to give a single-stranded nucleic acid. The means therefor may be a thermal treatment, a chemical denaturation or an enzymatic treatment. Preferably, it is a thermal treatment.

In the step B, said single-stranded nucleic acid is made to react with four kinds of DNTP (DATP, dGTP, dCTP and dTTP or dUTP) and primers with regular and inverted directions having complementary base sequences to the target nucleic acid in a buffer solution containing a thermostable DNA polymerase so that said primers are annealed to the single-stranded nucleic acid to conduct a primer extention reaction.

A primer with a regular direction and that with an inverted direction having complementary base sequences to the target nucleic acid are oligonucleotides having a base sequence which is complementary to one of target nucleic acid and is homologous to another. Accordingly, one primer may be complementary to another primer elongate.

Preferred buffer solutions containing a thermostable DNA polymerase are Tris buffers containing divalent cation such as magnesium ion.

An example of the conditions for conducting an elongation reaction by annealing the primer is a method in which a cycle of 98° C./1 second-1 minute and 68° C./1 second-10 minutes is repeated for 30 times.

The step of separating an elongated primer for making a single strand in the step C may be a thermal treatment, a chemical treatment or an enzymatic treatment. Preferably, it is a thermal treatment or an enzymatic treatment using RNase.

In the step D, the above-mentioned steps B and C are repeated. To be more specific, it is preferred that heating and cooling of 98° C./20 seconds and 68° C./30 seconds are repeated at least for 30 cycles.

An amplifying method of the present invention is applicable to a PCR for amplifying a DNA of 20 kb or more (hereinafter, referred to as a long-PCR) as well. In this long-PCR, advantages of both high DNA extension rate of Taq polymerase and high fidelity in DNA synthesis caused by a 3'–5' exonuclease activity of Pfu polymerase are necessary and both enzymes are used after mixing them. In this case, there is a question on a stability when both enzymes are stored in the same container because of the difference between their thermostabilities and that between the compositions of their stored solutions. However, in the DNA polymerase derived from a hyperthermophilic archaeon strain KOD1, a single enzyme exhibits both high DNA extension rate and high fidelity due to its 3',–5' exonuclease activity whereby it is possible that a long-PCR can be conducted by its sole use.

In the present invention, the amplified product produced by the above-mentioned amplification such as a labeled probe is used whereby a target nucleic acid can be detected.

Labeled probe is an oligonucleotide having a base sequence which is complementary to a target nucleic acid and is bonded with a labeled substance or a labeled binding substance.

Examples of the labeled substance are enzymes such as alkaline phosphatase, peroxidase and galactosidase, fluorescent substances and radioactive substances while examples of the labeled binding substances are biotin and digoxigenin. Labeled substance may be bonded via biotin, digoxigenin or avidin.

A method of introducing those labels into a probe is that, during the synthesis of oligonucleotide, DNTP to which those labeled substances or labeled binding substances are bonded is used as one of the components of dNTP whereby a synthesis is conducted.

Examples of detecting a nucleic acid bonded with a labeled probe are conventionally known methods such as a Southern hybridization and a Northern hybridization. In those methods, the fact that a hybrid is formed when single-stranded DNA and RNA are complementary each other is utilized whereby unknown nucleic acid fraction group is subjected to an agarose electrophoresis to separate its size, then the nucleic acid fraction in the gel is subjected, for example, to an alkali treatment, the resulting single strand is transferred to a filter, immobilized and hybridized with a labeled probe.

As to a detection of the label in case an alkaline phosphatase is used as a labeled substance, when a chemoluminescent substrate such as a 1,2-dioxetane compound (PPD) is made to react therewith, only nucleic acid forming a hybrid is illuminated. This is sensitized to an X-ray film whereby the size of the target nucleic acid and its position on electrophoresis can be confirmed.

A reagent kit for nucleic acid amplification according to the present invention contains primers of regular and inverted directions having base sequences complementary to target nucleic acid, four kinds of DNTP, divalent cation, thermostable DNA polymerase having a DNA extension rate of at least 30 bases/second and having a 3'–5' exonuclease activity and a buffer solution.

An example of divalent cation is magnesium ion. Its concentration is preferably about 1–3 mM. Examples of the buffer solution are tris buffer (pH 6.5, 75° C.) and tricine buffer (pH 6.5, 75° C.).

A specific example of the composition is as follows.

20 mM Tris-HCl (pH 6.5, 75° C.)

10 mM KCl 6 mM $(NH_4)_2SO_4$

1–3 mM $MgCl_2$ 0.1% Triton X-100

10 $\mu$g/ml BSA

20–200 $\mu$M dNTPs 0.1 $\mu$M–1 $\mu$M primer 0.1–250 ng template DNA.

A reagent kit for nucleic acid amplification according to the present invention contains a nucleic acid amplifying reagent comprising primers of regular and inverted directions having base sequences complementary to target nucleic acid, four kinds of dNTP, divalent cation, thermostable DNA polymerase having a DNA extension rate of at least 30 bases/second and having a 3'–5' exonuclease activity and a buffer solution for amplification, a target nucleic acid probe and a buffer for detection. The buffer for detection is that the detecting reagent varies depending upon the label. For example, it includes a color reagent or a luminous reagent.

KOD1 which is a kind of hyperthermophilic archaeon used in the present invention is a strain isolated from a solfatara at a wharf on Kodakara Island, Kagoshima.

Mycological properties of said strain are as follows.

Shape of cells: coccus, diplococcus; having flagella.

Temperature range for the growth: 65–100° C.

Optimum temperature for the growth: 95° C.

pH range for the growth: 5–9

Optimum pH: 6

Optimum salt concentration: 2–3%

Auxotrophy: heterotrophic

Oxygen demand: aerophobic

Cell membrane lipids: ether type

GC content of DNA: 38%

The hyperthermophilic archaeon strain KOD1 was a coccus having a diameter of about 1 $\mu$m and had plural polar flagella. From the mycological properties of the strain, its close relationship with Pfu DNA polymerase-productive bacterium (*Pyrococcus furiosus*) and with Tli (Vent) DNA polymerase-productive bacterium (*Thermococcus litoralis*) was suggested.

Cloning of the thermostable DNA polymerase gene of the present invention is carried out as follows.

Thus, the cloning method is that a primer is designed and synthesized depending upon an amino acid sequence in a conserved region of Pfu DNA polymerase (Nucleic Acids Research, 1993, vol.21, No.2, 259–265).

First, a PCR is conducted using the above-prepared primers (e.g., SEQ ID Nos.7 and 8) taking chromosomal DNA of the hyperthermophilic archaeon strain KOD1 as a template to amplify the DNA fragment. The DNA sequence (e.g., SEQ ID No.9) of the amplified fragment is determined and, after confirming that the originally set amino acid sequence is coded for, a Southern hybridization is conducted to the cleaved product of the chromosomal DNA with a restriction enzyme using said fragment as a probe. It is preferred that the approximate size of the fragment containing the aimed DNA polymerase gene is limited to about 4–7 Kbp.

Then DNA fragment of about 4–7 Kbp is recovered from the gel, a DNA library is prepared by Escherichia coli using said fragment and a colony hybridization is carried out using the above-mentioned PCR-amplified DNA fragment (e.g., SEQ ID No.9) to collect a clone strain.

The DNA polymerase gene of the strain KOD1 cloned in the present invention is composed of 5010 bases (estimated numbers of amino acids: 1670) (SEQ ID No.5).

Upon comparison with other DNA polymerases, there is a conserved region of ADNA polymerase which is an eukaryote type (Regions 1–5) in the gene of the present invention. In addition, there are EXO 1,2,3 which are 3'→5' exonuclease motive at the N terminal of said gene. In the conserved regions (Regions 1, 2) of the thermostable DNA polymerase gene derived from the hyperthermophilic archaeon strain KOD1, each of the intervening sequences is present and they are connected in a form where the open reading frame (ORF) is conserved.

When the thermostable DNA polymerase gene of the hyperthermophilic archaeon strain KOD1 is compared with Pfu DNA polymerase gene derived from *Pyrococcus furiosus* (Japanese Laid-Open Patent Publication Hei-05/328969) and with Tli (Vent) DNA polymerase gene derived from *Thermococcus litoralis* (Japanese Laid-Open Patent Publication He-06/7160) which are known enzymes, intervening sequence is present in the gene of the strain KOD1 of the present invention while there is no intervening sequence in the gene of the above-mentioned Pfu DNA polymerase and, in the Tli DNA polymerase gene, there are two kinds of intervening sequences but they are present within Regions 2 and 3 which are conserved regions and that greatly differs from the location where the intervening sequence in the thermostable DNA polymerase gene of KOD1 strain of the present invention exists (Refer to FIG. 7).

The gene of the present invention is a DNA which codes for the DNA polymerase derived from the hyperthermophilic archaeon strain KOD1. An example of said DNA contains a base sequence which codes for the amino acid sequence mentioned in SEQ ID No. 1 or 5. Further, such a DNA contains a base sequence mentioned in SEQ ID No. 5 or 6 or a part thereof.

In order to express the thermostable DNA polymerase derived from the hyperthermophilic archaeon strain KOD1 of the present invention in *Escherichia coli,* the intervening sequences of 1374–2453 bp and 2708–4316 bp in the base sequence shown by SEQ ID No.5 are removed by means of a PCR gene fusion to construct a DNA polymerase gene of a complete form. To be specific, a PCR is conducted on a cloned gene containing the intervening sequence by a combination of three pairs of primers to amplify the three fragments which are divided by the intervening sequence. In designing the primers used here, a part of the fragment which is to be bonded to its terminal is contained in its 5'-end. Then a PCR is conducted using the fragments to be bonded utilizing the duplicated sequence of the terminal whereby each of the fragments is bonded. Further PCR is conducted by the same manner using the resulting two kinds of fragments to give a DNA polymerase gene in a complete form containing no DNA polymerase gene derived from the strain KOD1 containing no intervening sequence.

Any vector may be used in the present invention so far as it makes cloning and expression of the thermostable DNA polymerase derived from KOD1 possible and its example is phage and plasmid. An example of the plasmid is a plasmid vector wherein an expression induced by T7 promoter is possible such as pET-8c. Other examples of the plasmid are pUC19, pBR322, pBluescript, pSP73, pGW7, pET3A and pET11C and so on. Examples of the phage are lambda gt11, lambda DASH and lambda ZapII and so on.

Examples of the host cell used in the present invention are *Escherichia coli* and yeasts. Examples of *Escherichia coli* are JM109, 101, XL1, PR1 and BL21(DE3)pysS and so on.

In the present invention, the gene coding for the thermostable DNA polymerase derived from the above-mentioned KOD1 is inserted into the above-mentioned vector to give a recombinant vector and the host cell is subjected to a transformation using said recombinant vector.

In the producing method of the present invention, the above-mentioned recombinant host cell is cultured whereby the thermostable DNA polymerase gene derived from the strain KOD1 is induced and expressed. The culture medium used for the culture of the recombinant host cell and the condition therefor follow the conventional methods.

In a specific example, *Escherichia coli* which is transformed by pET-8c plasmid containing a DNA polymerase gene in a complete form containing no intervening sequence derived from the strain KOD1 is cultured, for example, in a TB medium whereby an induction treatment is conducted. It is preferred that the induction treatment of T7 promoter is carried out by addition of isopropylthio-β-D-galactoside.

The purifying method of the present invention includes, after culturing the recombinant host cells , a step wherein (a) recombinant host cells are collected, disintegrated and the cell extract is prepared and a step wherein (b) impure protein derived from the host cells is removed.

The thermostable DNA polymerase which is produced from the recombinant host cells is separated and recovered from the culture liquid by means of centrifugation or the like after culturing the host bacterial cells in a medium followed by inducing. After said bacterial cells are resuspended in a buffer, they are disintegrated by means of ultrasonic treatment, Dyno mill, French press, etc. Then a thermal treatment is conducted and the heat stable DNA polymerase is recovered from the supernatant fluid. In disintegrating the bacterial cells, ultrasonic treatment, Dyno mill and French press method are preferred.

A thermal treatment is preferred as one of the steps for removing the impure protein derived from the host cells. The condition for the thermal treatment is at 70° C. or higher or, preferably, at 90° or higher. Other means for removing the impure protein are various chromatographic techniques.

Molecular weight of the thermostable DNA polymerase derived from the hyperthermophilic archaeon strain KOD1 obtained as such is about 90 KDa (cf. FIG. 5).

When a polymerase chain reaction is conducted using said thermostable DNA polymerase, a sufficient amplification of the aimed DNA fragments is confirmed (cf. FIG. 6).

Now the present invention will be illustrated by referring partly to the drawings wherein:

FIG. 2 is a photographic picture of electrophoresis as a substitute for a drawing and shows the comparison of the DNA extension rate of various thermostable DNA polymerases in which FIG. 2*a* shows the cases of KOD polymerase and Pfu polymerase while

FIG. 3 is a photographic picture of electrophoresis as a substitute for a drawing and shows the comparison of the PCR due to the difference in the reaction time of various thermostable DNA polymerase;

Figure 6:
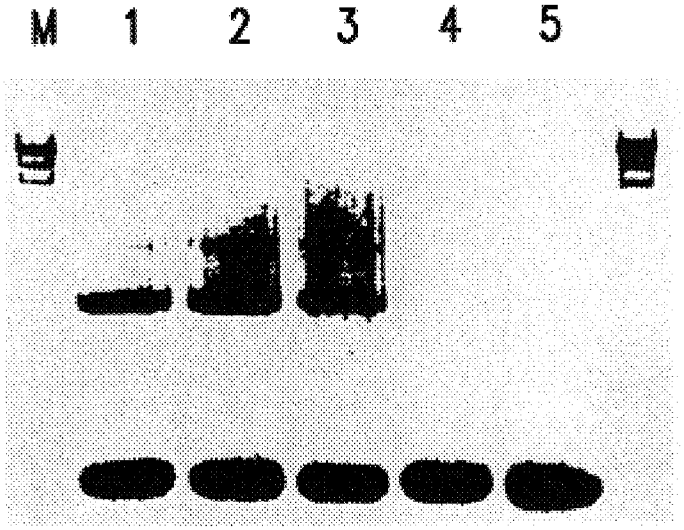
Figure 7:
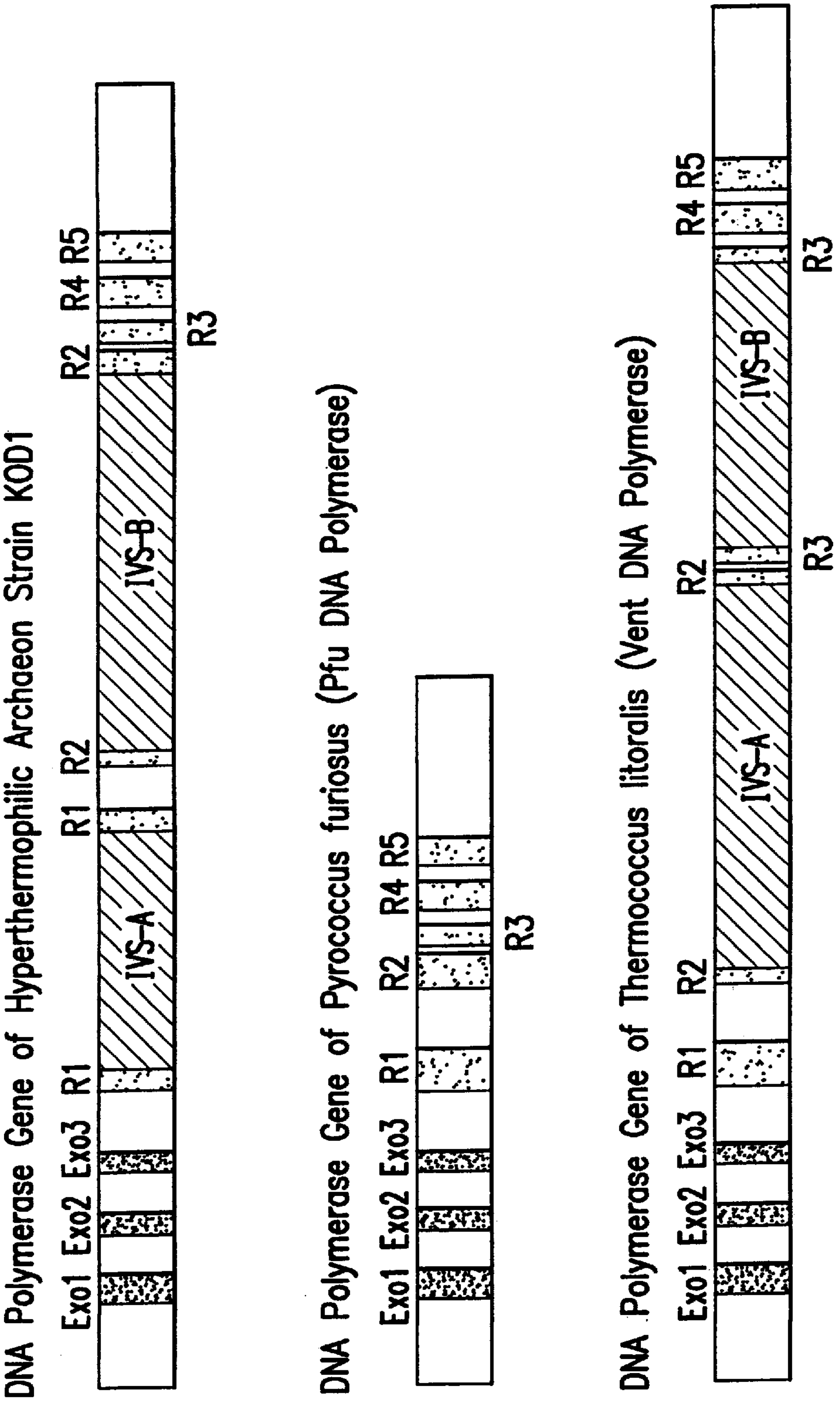

FIG. 6 is a photographic picture of electrophoresis as a substitute for a drawing and shows the result of the PCR by the thermostable DNA polymerase derived from KOD1; and FIG. 7 is drawings which show a comparison of the DNA polymerase gene derived from the hyperthermophilic archaeon strain KOD1 with the thermostable DNA polymerase gene derived from *Pyrococcus furiosus* and that derived from *Thermococcus litoralis* which are thought to be similar bacteria.

EXAMPLE 1

Cloning of DNA Polymerase Gene Derived from Hyperthermophilic Archaeon Strain KOD1

The hyperthermophilic archaeon strain KOD1 isolated in Kodakara Island, Kagoshima was cultured at 95° C. and then the bacterial cells were recovered. Chromosomal DNA of the hyperthermophilic archaeon strain KOD1 was prepared by a conventional method from the resulting bacterial cells.

Two kinds of primers (5'-GGATTAGTATAGTGCCAATGGAAGGCGAC-3' [SEQ ID No.7] and 5'-GAGGGCGAAGTTTATTCCGAGCTT-3' [SEQ ID No.8]) were synthesized based upon the amino acid sequence at the conserved region of the DNA polymerase (Pfu polymerase) derived from *Pyrococcus furiosus*. A PCR was carried out using those two primers where the prepared chromosomal DNA was used as a template.

After the base sequence (SEQ ID No.9) of the PCR-amplified DNA fragment was determined and the amino acid sequence (SEQ ID No.10) was determined, a Southern hybridization was conducted using said amplified DNA fragment to the product of the strain KOD1 chromosomal DNA treated with a restriction enzyme whereby the size of the fragment coding for the DNA polymerase was calculated (about 4–7 Kbp). Further, the DNA fragment of this size was recovered from agarose gel, inserted into a plasmid pBS (manufactured by Stratgene) and *Escherichia coli* (*E. coli* JM 109) was transformed by this mixture to prepare a library.

A colony hybridization was conducted using a probe (SEQ ID No.9) used for the Southern hybridization to obtain a clone strain (*E. coli* JM109/pBSKOD1) which is thought to contain the DNA polymerase gene derived from strain KOD1.

EXAMPLE 2

Determination of Base Sequence of the Clone Fragment

A plasmid pBSKOD1 was recovered from the clone strain *E. coli* JM109/pBSKOD1 obtained in Example 1 and its base sequence (SEQ ID No.5) was determined by a conventional method. Further, the amino acid sequence was presumed from the determined base sequence. The DNA polymerase gene derived from KOD1 strain comprised 5010 bases wherein 1670 amino acids were coded.

EXAMPLE 3

Construction of Recombinant Expression Vector

In order to prepare a complete polymerase gene, the intervening sequence parts at two places (1374–2453 bp and 2708–4316 bp) were removed by a PCR fusion method. In the PCR fusion method, three pairs of primers (SEQ ID Nos.11–16) were combined using a primer recovered from the clone strain as a template and a PCR was conducted for each of them to amplify three fragments wherefrom the intervening sequences were removed. At that time, the primer used for the PCR was designed in such a manner that the side which binds to another fragment has the same sequence as the binding partner has. In addition, a design was conducted in such a manner that different restriction enzyme sites (EcoRV at N-terminal while BamHI at C-terminal) were created at both ends.

After that, among the PCR-amplified fragments, that which located at the central part of the structure and that which is located at the N-terminal side are mixed and a PCR was conducted using each of the fragments as a primer. At the same time, the fragment located at the central part of the structure and that located at the C-terminal side are mixed and a PCR was conducted using each of the fragments as a primer. Two kinds of fragments obtained as such were subjected to a PCR once again to give gene fragments in a complete form having no intervening sequence, having EcoRV and BamHI sites at the N- and C-terminals, respectively and coding for the DNA polymerase derived from strain KOD1.

Further, said gene was subcloned using an expression vector which can be induced by T7 promoter, an NcoI/BamHI site of pET-8c and the previously-created restriction enzyme site to give a recombinant expression vector (pET-pol).

EXAMPLE 4

Expression and Purification of DNA Polymerase Derived from KOD1

*Escherichia coli* (BL21(DE3)) was transformed using a recombinant expression vector (pET-pol) obtained in Example 3, the resulting transformant was cultured in a TB medium (mentioned in Molecular Cloning, p.A.2, 1989) and, at one hour before collecting the bacterial cells, an induction treatment of T7 promoter was conducted by addition of isopropylthio-β-D-galactopyrenoside. Bacterial cells were recovered from the cultured liquid by means of centrifugation. They were resuspended in a buffer and disintegrated by an ultrasonic treatment to give a cell extract. In order to remove the impure protein derived from the host cells, the disintegrated cell solution was treated at 94° C. for 20 minutes whereby the impure protein derived from the host cells trifugation to give a thermostable DNA polymerase derived from strain KOD1.

The *Escherichia coli* BL21 (DE3) pER-pol was deposited on Apr. 22, 1996 under the Budapest Treaty at National Institute of Bioscience and Human-Technology Agency of Industrial Science and Technology (1–3, Higashi 1 chome Tsukuba-shi Ibaraki-ken 305, JAPAN) in accordance with the Budapest Treaty under the accession number FERM BP-5513.

EXAMPLE 5

Purification of Thermostable DNA Polymerase Derived from KOD1

Figure 5:
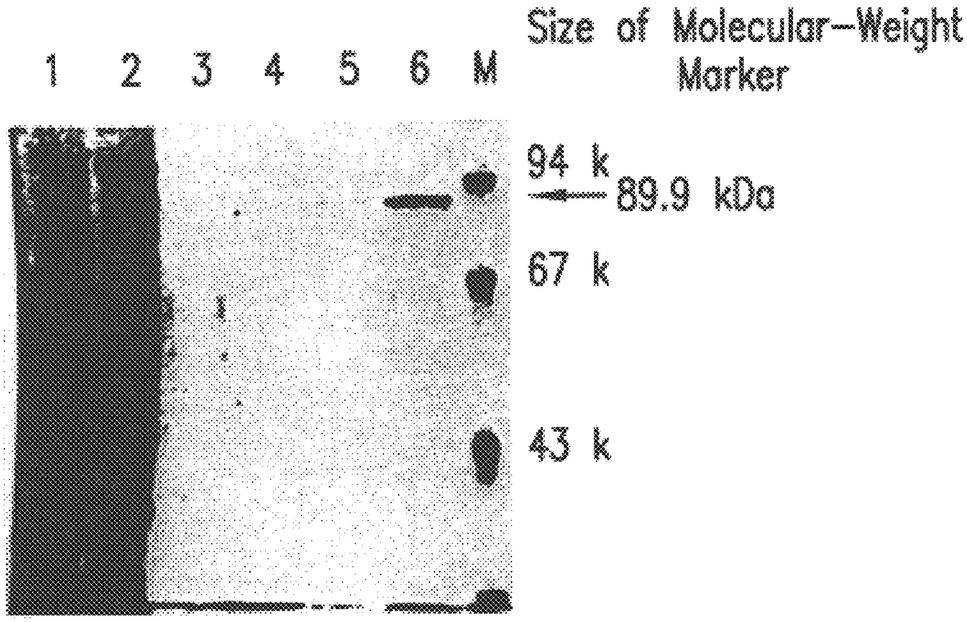
FIG. 5 is a photographic picture of electrophoresis as a substitute for a drawing and shows the result of the measurement of molecular weight of the thermostable DNA polymerase derived from KOD1.

Molecular weight of the thermostable DNA polymerase derived from KOD1 obtained in Example 4 was calculated by means of an SDS-PAGE method whereby it was found to be about 86–92 kDa (FIG. 5). Further, a PCR was conducted using the thermostable DNA polymerase derived from KOD1 obtained in Example 4 and the known template primer whereupon a DNA fragment which was to be a target was confirmed (FIG. 6) by the same manner as in the case where the thermostable DNA polymerase derived from *Thermococcus litoralis* was used and a high thermostable DNA polymerase activity was confirmed.

Comparative Example 1

Comparison with the Thermostable DNA Polymerase Gene Derived from *Pyrococcus furiosus* or from *Thermococcus litoralis* which are to be Similar to the Hyperthermophilic archaeon strain KOD1 of the Present Invention Amino acid sequences were estimated from the DNA sequences of the DNA polymerase gene derived from the hyperthermophilic archaeon strain KOD1 of the present invention (SEQ ID No.6), the thermostable DNA polymerase gene derived from *Pyrococcus furiosus* (Japanese Laid-Open Patent Publication Hei-5/328969) and the thermostable DNA polymerase gene derived from *Thermococcus litoralis* (Japanese Laid-Open Patent Publication Hei-6/7160) and were compared and investigated.

In the DNA polymerase derived from KOD1 of the present invention, there was Regions 1–5 which were the conserved regions of αDNA polymerase of an eurokaryotic type. Further, there were EXO1, 2 and 3 which were 3'→5' exonuclease motives at the N-terminal side. However, in each of the Region 1 and Region 2 which were the αDNA polymerase conserved regions, there were intervening sequences IVS-A and IVS-B (refer to FIG. 7).

On the other hand, in Pfu polymerase which is a thermostable DNA polymerase derived from *Pyrococcus furiosus,* there was no intervening sequence. In the case of Vent polymerase which is a thermostable DNA polymerase derived from *Thermococcus litoralis,* there were the intervening sequences (IVS1 and IVS2) in the αDNA polymerase conserved regions (Region 2 and Region 3) (refer to FIG.7).

EXAMPLE 6

Measurement of DNA Extension Rate of the DNA Polymerase Derived from Hyperthermophilic Archaeon Strain KOD1

DNA prepared by annealing the M13mp18DNA with M13P7 primer having a base sequence as mentioned in SEQ ID No.2 was used as a substrate and the rate of synthesizing the DNA in a reaction buffer solution [20 mM Tris-HCl (pH 7.5 at 75° C.), 10 mM KCl, 6 mM $(NH_4)_2SO_4$, 2 mM $MgCl_2$, 0.1% Triton X-100 and 10 μg/ml nuclease-free BSA] containing the DNA polymerase derived from the hyperthermophilic archaeon strain KOD1 manufactured in Examples 1–5 was investigated for the reaction time of 20, 40, 60, 80 and 100 seconds (FIG. 1) or 40, 60, 80 and 100 seconds (FIG. 2). The results are given in FIG. 1 and in FIG. 2.

A part of the DNA sample during the elongation reaction was taken out for each reaction time and was added to a reaction stopping solution (60 mM EDTA, 60 μM NaOH, 0.1% BPB and 30% glycerol) in the same amount.

The DNA samples obtained in the above process were separated and analyzed by means of an alkaline agarose electrophoresis and the size of the synthesized DNA was checked.

Figure 1:
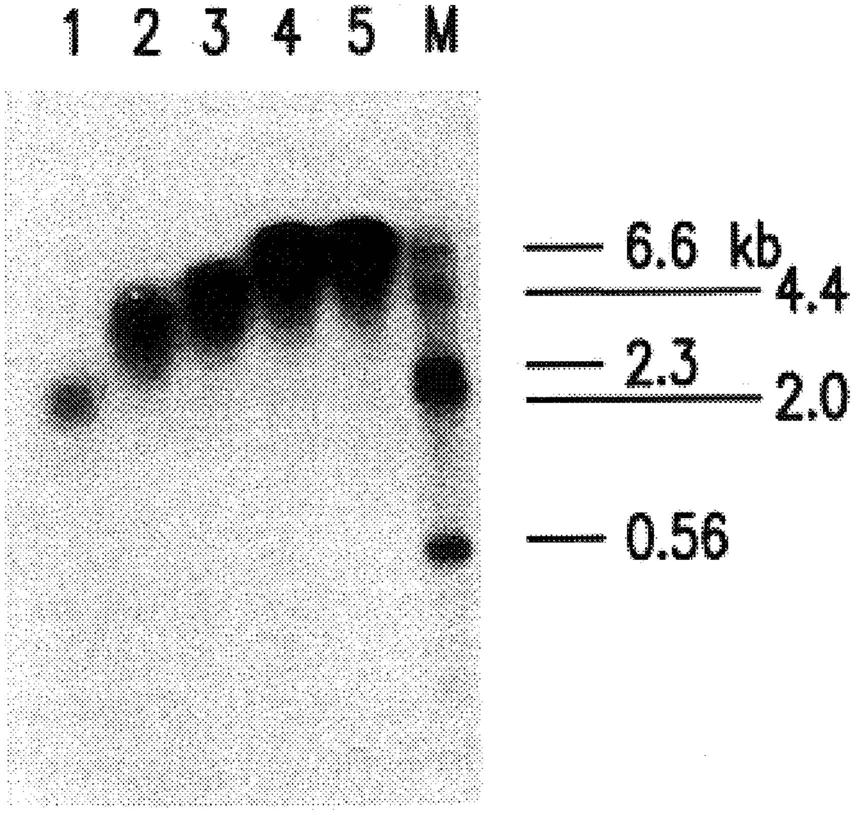
FIG. 1 is a photographic picture of electrophoresis as a substitute for a drawing and shows the result of the measurement of the DNA extension rate of the KOD polymerase.

1, 2, 3, 4 and 5 in FIG. 1 show the results of the reactions for 0.3 minute (20 seconds), 0.7 minute (40 seconds), 1 minute (60 seconds), 1.3 minutes (80 seconds) and 1.7 minutes (100 seconds), respectively. It is apparent from FIG. 1 that the DNA extension rate of the DNA polymerase derived from the hyperthermophilic archaeon strain KOD1 was 105 bases/second.

1, 2, 3 and 4 in FIG. 2 show the results of the reaction for 0.7 minute (40 seconds), 1 minute (60 seconds), 1.3 minutes (80 seconds) and 1.7 minutes (100 seconds), respectively. It is apparent from FIG. 2 that the DNA extension rate of the DNA polymerase derived from the hyperthermophilic archaeon strain KOD1 was 138 bases/second.

Figure 2A:
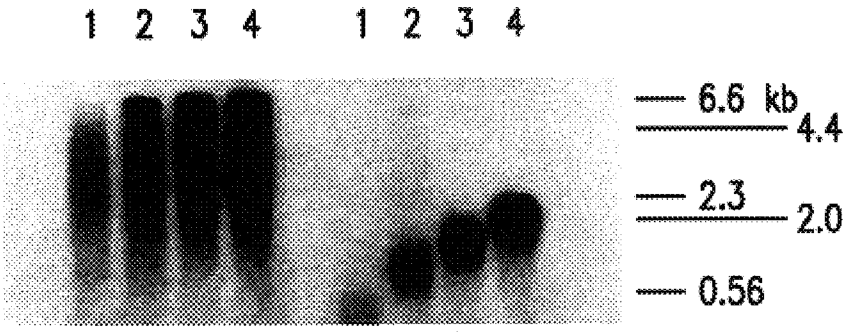
Figure 2B:
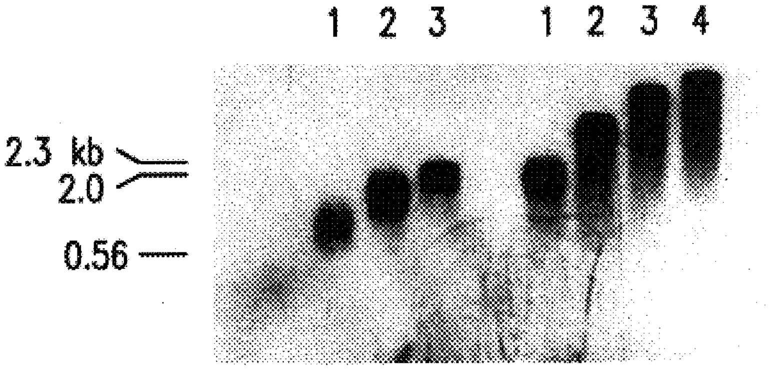
FIG. 2*b* shows the cases of Deep Vent polymerase and Taq polymerase.
Figure 4:
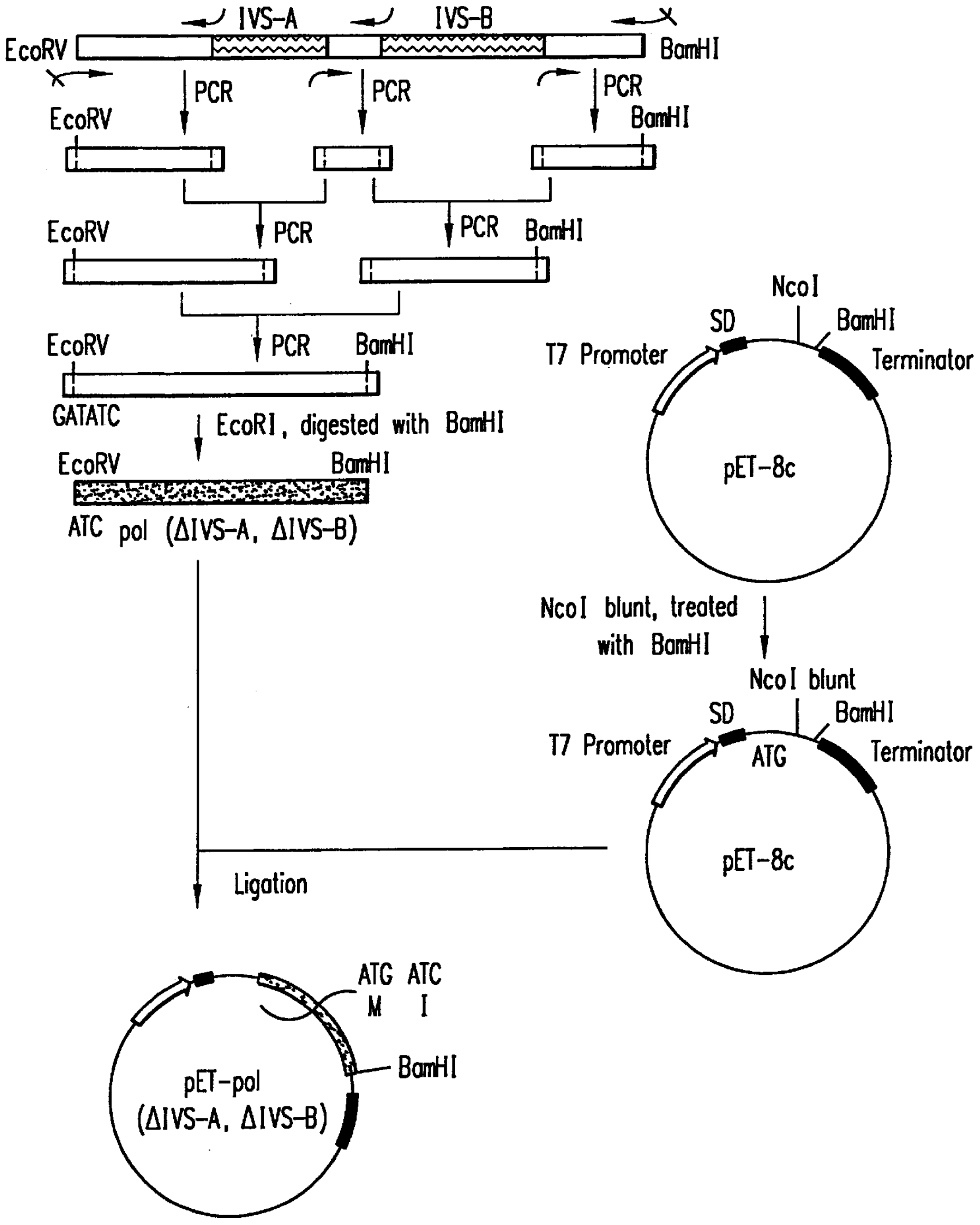
FIG. 4 shows the constructive charts of the recombinant expression vector.

On the other hand, the DNA synthesizing rate of each of Pfu polymerase (Stratgene), Deep Vent polymerase (New England Biolabo) and Taq polymerase (Takara Shuzo) was measured by the same manner in each of the buffers therefor (FIG. 2*a* and FIG. 2*b*). The DNA extension rates of those DNA polymerases were 24.8 bases/second for Pfu polymerase, 23.2 bases/second for Deep Vent polymerase and 61.0 bases/second for Taq polymerase.

From the above results, it was suggested that the DNA extension rate of the DNA polymerase derived from the hyperthermophilic archaeon strain KOD1 was about six-fold of those of Pfu polymerase and Deep Vent polymerase and about two-fold of that of Taq polymerase.

EXAMPLE 7

Measurement of Fidelity of the DNA Polymerase Derived from the Hyperthermophilic archaeon strain KOD1 in the Reaction for the Synthesis of DNA A rate for resulting in an error in the DNA synthesis was measured by a method of Kunkel (Kunkel, 1985, Journal of Biological Chemistry, 260, 5787–5796). In this method, a DNA synthesis reaction was conducted using a DNA polymerase derived from the hyperthermophilic archaeon strain KOD1 manufactured in Examples 1–5 using an M13mp18DNA having a gap at a laqZ part containing a part of the genes coding for β-galactosidase as a substrate and transfected to *E. coli* JM109 in an NZY medium containing 5-bromo-4-chloro-3-indolyl-β-D-galactoside and isopropyl-thio-β-D-galactoside using an M13mp18DNA in which lacZ part was double-stranded.

When β-galactosidase wherein a function is lost or lowered was expressed due to a reading error or a frame shift during the synthetic reaction of DNA, it is not possible to utilize 5-bromo-4-chloro-3-indolyl-β-D-galactoside whereupon the color of plaque becomes colorless or light blue. On the other hand, when there is no error in the synthesized DNA and a complete β-galactosidase was expressed, plaque becomes blue. The rate of induction of error was measured in the DNA synthesis from the rate of the sum of colorless and light blue plaque to the total plaque.

The rate of induction of error in the DNA synthesis was also measured for Pfu polymerase (Stratgene), Taq polymerase (Takara Shuzo) and delta Tth polymerase (Toyobo) which were made to react by the same manner.

Further, the rate of induction of error in the DNA synthesis was also measured for a mixture of Taq polymerase and Pfu polymerase. The results are given in Table 1.

TABLE 1

Measurement of Fidelity in the Reaction of DNA Synthesis of DNA Polymerase Derived from Hyperthermophilic archaeon strain KOD1

| Enzyme | Light Blue | White | Mutant | Total | Mutant Frequence($10^{-4}$) |
|---|---|---|---|---|---|
| KOD1 pol. | 12 | 11 | 23 | 6619 | 37.7 |
| Pfu | 15 | 15 | 30 | 7691 | 39.0 |
| Taq | 30 | 24 | 54 | 4141 | 130 |
| ΔTth | 70 | 45 | 115 | 7375 | 156 |
| Taq/Pfu(20:1) | 10 | 20 | 30 | 4238 | 63.7 |
| Taq/Pfu(50:1) | 10 | 13 | 23 | 4489 | 53.5 |

It is apparent from Table 1 that the fidelity of the DNA polymerase derived from hyperthermophilic archaeon strain KOD1 in the DNA synthesis reaction is suggested to be superior to Taq polymerase and same as Pfu polymerase. In addition, a mixture of Taq polymerase and Pfu polymerase exhibits a medium fidelity that it is superior to Taq polymerase and inferior to Pfu polymerase.

EXAMPLE 8

Comparison in PCR of Various Thermostable DNA Polymerases by the Difference in the Reaction Time lambda-DNA (3 μg) was used as a target nucleic acid; oligo-nucleotides having a sequence as mentioned in SEQ ID Nos. 3 and 4 were used as primers; and a buffer containing 20 mM Tri-HCl (pH 7.5 at 75° C.), 10 mM KCl, 6 mM $(NH_4)_2SO_4$, 2 mM $MgCl_2$, 0.1% Triton X-100, 10 μg/ml BSA and 200 μM dNTPs was used as a buffer. DNA polymerase derived from hyperthermophilic archaeon strain KOD1 (KOD polymerase), Taq polymerase which is widely used for PCR and Pfu polymerase which exhibits 3'–5' exonuclease activity were also used as the thermostable DNA polymerases. The used titer of each polymerase was 2 units.

A PCR amplification reaction was conducted using a DNA Thermal Cycler (Perkin-Elmer) in a schedule wherein a cycle comprising 94° C./20 seconds and 68° C./x second (x: reaction time) was repeated for 30 times. In the case of the DNA polymerase derived from the hyperthermophilic archaeon strain KOD1 (KOD polymerase), amplification of the target DNA was confirmed by conducting 30 cycles of 94° C./20 seconds-68° C./1 second while, in the case of Taq polymerase, amplification of DNA was first confirmed by conducting 30 cycles of 94° C./20 seconds-68° C./10 seconds. In the case of Pfu polymerase, amplification of DNA was at least confirmed by conducting 30 cycles of 94° C./20 seconds-68° C./1 minute. The results are given in FIG. 3.

In the present invention, it is possible to amplify the DNA with a high fidelity within a short reaction time when a DNA polymerase derived from hyperthermophilic archaeon strain KOD1 which is a thermostable DNA polymerase having at least 30 bases/second of DNA extension rate and having a 3'–5' exonuclease activity. When this method is made into a form of a kit, it is possible to improve the simplicity and convenience. In addition, when only kind of thermostable DNA polymerase having both high extension rate (at least 30 bases/second) which has not been available yet and 3'–5' exonuclease activity is used, it is possible to shorten the time for the primer extention reaction and to amplify the relatively big product with a high fidelity.

What we claim is:

1. A reagent kit for amplifying target nucleic acid which comprises primers, wherein said primers are selected so as to be sufficiently complementary to different strands of target nucleic acid to anneal therewith, four kinds of dNTP, divalent cation, thermostable DNA polymerase having a DNA extension rate of at least 30 bases/second and a 3'–5' exonuclease activity and buffer solution.

2. The reagent kit of claim 1, wherein said thermostable DNA polymerase is an enzyme obtainable from a hyperthermophilic archaeon strain.

3. The reagent kit of claim 1, wherein said thermostable DNA polymerase is an enzyme having the following physical and chemical properties:

Action: It catalyses the extension reaction of nucleotide sequence that is complementary to a template nucleotide sequence, using nucleotide triphosphate as substrate and it has a 3'–5' exonuclease activity, DNA extension rate: at least 30 bases/second Optimum pH: 6.5–7.5 (at 75° C.)

Optimum temperature: 75° C.

Molecular weight: about 88–90 Kda

Amino acid sequence: SEQ ID No. 1.

4. A reagent kit for detecting target nucleic acid which comprises primers, wherein said primers are selected so as to be sufficiently complementary to different strands of target nucleic acid to anneal therewith, four kinds of dNTP, divalent cation, thermostable DNA polymerase having a DNA extension rate of at least 30 bases/second and a 3'–5' exonuclease activity, amplifying buffer solution, a probe capable of hybridizing with amplified nucleic acid and a detection buffer solution.

5. The reagent kit of claim 4, wherein said thermostable DNA polymerase is an enzyme obtainable from a hyperthermophilic archaeon strain.

6. The reagent kit of claim 4, wherein said thermostable DNA polymerase is an enzyme having the following physical and chemical properties;

Action: It catalyses the extension reaction of nucleotide sequence that is complementary to a template nucleotide sequence, using nucleotide triphosphate as substrate and it has a 3'–5' exonuclease activity, DNA extension rate: at least 30 bases/second Optimum pH: 6.5–7.5 (at 75° C.)

Optimum temperature: 75° C.

Molecular weight: about 88–90 Kda

Amino acid sequence: as mentioned in SEQ ID No. 1.

* * * * *

UNITED STATES PATENT AND TRADEMARK OFFICE

CERTIFICATE OF CORRECTION

PATENT NO. : 6,225,065 B1
DATED : May 1, 2001
INVENTOR(S) : Masao Kitabayashi et al.

It is certified that error appears in the above-identified patent and that said Letters Patent is hereby corrected as shown below:

Column 2,
Line 9, before "activity" insert -- exonuclease --.

Column 41,
Line 17, after "buffer solution" insert -- wherein said thermostable DNA polymerase is an enzyme having an amino acid sequence of SEQ ID NO: 1 --.

Column 42,
Line 16, after "buffer solution" insert -- wherein said thermostable DNA polymerase is an enzyme having an amino acid sequence of SEQ ID NO: 1 --.
Line 33, delete "as mentioned in".

Signed and Sealed this

Eleventh Day of June, 2002

*Attest:*

JAMES E. ROGAN

*Attesting Officer* *Director of the United States Patent and Trademark Office*

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
(A) LENGTH: 774 amino acids
(B) TYPE: amino acid
(C) STRANDEDNESS: double
(D) TOPOLOGY: linear (ii) MOLECULE TYPE: protein (xi) SEQUENCE DESCRIPTION: SEQ ID NO: 1:

```
Met Ile Leu Asp Thr Asp Tyr Ile Thr Glu Asp Gly Lys Pro Val Ile
                 5                  10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
 65                  70                  75                  80

Glu Val Trp Lys Leu Tyr Phe Thr His Pro Gln Asp Val Pro Ala Ile
                 85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320
```

-continued

```
Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735
```

-continued

```
Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770


(2) INFORMATION FOR SEQ ID NO: 2:

     (i) SEQUENCE CHARACTERISTICS:
          (A) LENGTH: 24 base pairs
          (B) TYPE: nucleic acid
          (C) STRANDEDNESS: double
          (D) TOPOLOGY: linear

    (ii) MOLECULE TYPE: other nucleic acid

    (xi) SEQUENCE DESCRIPTION: SEQ ID NO: 2:

CGCCAGGGTT TTCCCAGTCA CGAC                                            24


(2) INFORMATION FOR SEQ ID NO: 3:

     (i) SEQUENCE CHARACTERISTICS:
          (A) LENGTH: 20 base pairs
          (B) TYPE: nucleic acid
          (C) STRANDEDNESS: double
          (D) TOPOLOGY: linear

    (ii) MOLECULE TYPE: other nucleic acid

    (xi) SEQUENCE DESCRIPTION: SEQ ID NO: 3:

GGGCGGCGAC CTCGCGGGTT                                                 20


(2) INFORMATION FOR SEQ ID NO: 4:

     (i) SEQUENCE CHARACTERISTICS:
          (A) LENGTH: 24 base pairs
          (B) TYPE: nucleic acid
          (C) STRANDEDNESS: double
          (D) TOPOLOGY: linear

    (ii) MOLECULE TYPE: other nucleic acid

    (xi) SEQUENCE DESCRIPTION: SEQ ID NO:4:

GCCCATAATA ATCTGCCGGT CAAT                                            24


(2) INFORMATION FOR SEQ ID NO: 5:

     (i) SEQUENCE CHARACTERISTICS:
          (A) LENGTH: 5342 base pairs
          (B) TYPE: nucleic acid
          (C) STRANDEDNESS:  double
          (D) TOPOLOGY:  linear

    (ii) MOLECULE TYPE: cDNA

    (vi) ORIGINAL SOURCE: Hyperthermophilic archaeon

    (xi) SEQUENCE DESCRIPTION: SEQ ID NO: 5:

GCTTGAGGGC CTGCGGTTAT GGGACGTTGC AGTTTGCGCC TACTCAAAGA TGCCGGTTTT     60

ATAACGGAGA AAAATGGGGA GCTATTACGA TCTCTCCTTG ATGTGGGGTT TACAATAAAG    120

CCTGGATTGT TCTACAAGAT TATGGGGGAT GAAAG ATG ATC CTC GAC ACT GAC       173
                                       Met Ile Leu Asp Thr Asp
                                                        5

TAC ATA ACC GAG GAT GGA AAG CCT GTC ATA AGA ATT TTC AAG AAG GAA      221
Tyr Ile Thr Glu Asp Gly Lys Pro Val Ile Arg Ile Phe Lys Lys Glu
```

-continued

```
             10                  15                  20

AAC GGC GAG TTT AAG ATT GAG TAC GAC CGG ACT TTT GAA CCC TAC TTC           269
Asn Gly Glu Phe Lys Ile Glu Tyr Asp Arg Thr Phe Glu Pro Tyr Phe
         25                  30                  35

TAC GCC CTC CTG AAG GAC GAT TCT GCC ATT GAG GAS GTC AAG AAG ATA           317
Tyr Ala Leu Leu Lys Asp Asp Ser Ala Ile Glu Glu Val Lys Lys Ile
     40                  45                  50

ACC GCC GAG AGG CAC GGG ACG GTT GTA ACG GTT AAG CGG GTT GAA AAG           365
Thr Ala Glu Arg His Gly Thr Val Val Thr Val Lys Arg Val Glu Lys
 55                  60                  65                  70

GTT CAG AAG AAG TTC CTC GGG AGA CCA GTT GAG GTC TGG AAA CTC TAC           413
Val Gln Lys Lys Phe Leu Gly Arg Pro Val Glu Val Trp Lys Leu Tyr
                 75                  80                  85

TTT ACT CAT CCG CAG GAC GTC CCA GCG ATA AGG GAC AAG ATA CGA GAG           461
Phe Thr His Pro Gln Asp Val Pro Ala Ile Arg Asp Lys Ile Arg Glu
             90                  95                 100

CAT GGA GCA GTT ATT GAC ATC TAC GAG TAC GAC ATA CCC TTC GCC AAG           509
His Gly Ala Val Ile Asp Ile Tyr Glu Tyr Asp Ile Pro Phe Ala Lys
        105                 110                 115

CGC TAC CTC ATA GAC AAG GGA TTA GTG CCA ATG GAA GGC GAC GAG GAG           557
Arg Tyr Leu Ile Asp Lys Gly Leu Val Pro Met Glu Gly Asp Glu Glu
    120                 125                 130

CTG AAA ATG CTC GCC TTC GAC ATT CAA ACT CTC TAC CAT GAG GGC GAG           605
Leu Lys Met Leu Ala Phe Asp Ile Gln Thr Leu Tyr His Glu Gly Glu
135                 140                 145                 150

GAG TTC GCC GAG GGG CCA ATC CTT ATG ATA AGC TAC GCC GAC GAG GAA           653
Glu Phe Ala Glu Gly Pro Ile Leu Met Ile Ser Tyr Ala Asp Glu Glu
                155                 160                 165

GGG GCC AGG GTG ATA ACT TGG AAG AAC GTG GAT CTC CCC TAC GTT GAC           701
Gly Ala Arg Val Ile Thr Trp Lys Asn Val Asp Leu Pro Tyr Val Asp
            170                 175                 180

GTC GTC TCG ACG GAG AGG GAG ATG ATA AAG CGC TTC CTC CGT GTT GTG           749
Val Val Ser Thr Glu Arg Glu Met Ile Lys Arg Phe Leu Arg Val Val
        185                 190                 195

AAG GAG AAA GAC CCG GAC GTT CTC ATA ACC TAC AAC GGC GAC AAC TTC           797
Lys Glu Lys Asp Pro Asp Val Leu Ile Thr Tyr Asn Gly Asp Asn Phe
    200                 205                 210

GAC TTC GCC TAT CTG AAA AAG CGC TGT GAA AAG CTC GGA ATA AAC TTC           845
Asp Phe Ala Tyr Leu Lys Lys Arg Cys Glu Lys Leu Gly Ile Asn Phe
215                 220                 225                 230

GCC CTC GGA AGG GAT GGA AGC GAG CCG AAG ATT CAG AGG ATG GGC GAC           893
Ala Leu Gly Arg Asp Gly Ser Glu Pro Lys Ile Gln Arg Met Gly Asp
                235                 240                 245

AGG TTT GCC GTC GAA GTG AAG GGA CGG ATA CAC TTC GAT CTC TAT CCT           941
Arg Phe Ala Val Glu Val Lys Gly Arg Ile His Phe Asp Leu Tyr Pro
            250                 255                 260

GTG ATA AGA CGG ACG ATA AAC CTG CCC ACA TAC ACG CTT GAG GCC GTT           989
Val Ile Arg Arg Thr Ile Asn Leu Pro Thr Tyr Thr Leu Glu Ala Val
        265                 270                 275

TAT GAA GCC GTC TTC GGT CAG CCG AAG GAG AAG GTT TAC GCT GAG GAA          1037
Tyr Glu Ala Val Phe Gly Gln Pro Lys Glu Lys Val Tyr Ala Glu Glu
    280                 285                 290

ATA ACA CCA GCC TGG GAA ACC GGC GAG AAC CTT GAG AGA GTC GCC CGC          1085
Ile Thr Pro Ala Trp Glu Thr Gly Glu Asn Leu Glu Arg Val Ala Arg
295                 300                 305                 310

TAC TCG ATG GAA GAT GCG AAG GTC ACA TAC GAG CTT GGG AAG GAG TTC          1133
Tyr Ser Met Glu Asp Ala Lys Val Thr Tyr Glu Leu Gly Lys Glu Phe
                315                 320                 325

CTT CCG ATG GAG GCC CAG CTT TCT CGC TTA ATC GGC CAG TCC CTC TGG          1181
```

-continued

```
Leu Pro Met Glu Ala Gln Leu Ser Arg Leu Ile Gly Gln Ser Leu Trp
            330                 335                 340

GAC GTC TCC CGC TCC AGC ACT GGC AAC CTC GTT GAG TGG TTC CTC CTC      1229
Asp Val Ser Arg Ser Ser Thr Gly Asn Leu Val Glu Trp Phe Leu Leu
        345                 350                 355

AGG AAG GCC TAT GAG AGG AAT GAG CTG GCC CCG AAC AAG CCC GAT GAA      1277
Arg Lys Ala Tyr Glu Arg Asn Glu Leu Ala Pro Asn Lys Pro Asp Glu
    360                 365                 370

AAG GAG CTG GCC AGA AGA CGG CAG AGC TAT GAA GGA GGC TAT GTA AAA      1325
Lys Glu Leu Ala Arg Arg Arg Gln Ser Tyr Glu Gly Gly Tyr Val Lys
375                 380                 385                 390

GAG CCC GAG AGA GGG TTG TGG GAG ACC ATA GTG TAC CTA GAT TTT AGA      1373
Glu Pro Glu Arg Gly Leu Trp Glu Asn Ile Val Tyr Leu Asp Phe Arg
                395                 400                 405

TGC CAT CCA GCC GAT ACG AAG GTT GTC GTC AAG GGG AAG GGG ATT ATA      1421
Cys His Pro Ala Asp Thr Lys Val Val Val Lys Gly Lys Gly Ile Ile
            410                 415                 420

AAC ATC AGC GAG GTT CAG GAA GGT GAC TAT GTC CTT GGG ATT GAC GGC      1469
Asn Ile Ser Glu Val Gln Glu Gly Asp Tyr Val Leu Gly Ile Asp Gly
        425                 430                 435

TGG CAG AGA GTT AGA AAA GTA TGG GAA TAC GAC TAC AAA GGG GAG CTT      1517
Trp Gln Arg Val Arg Lys Val Trp Glu Tyr Asp Tyr Lys Gly Glu Leu
    440                 445                 450

GTA AAC ATA AAC GGG TTA AAG TGT ACG CCC AAT CAT AAG CTT CCC GTT      1565
Val Asn Ile Asn Gly Leu Lys Cys Thr Pro Asn His Lys Leu Pro Val
455                 460                 465                 470

GTT ACA AAG AAC GAA CGA CAA ACG AGA ATA AGA GAC AGT CTT GCT AAG      1613
Val Thr Lys Asn Glu Arg Gln Thr Arg Ile Arg Asp Ser Leu Ala Lys
                475                 480                 485

TCT TTC CTT ACT AAA AAA GTT AAG GGC AAG ATA ATA ACC ACT CCC CTT      1661
Ser Phe Leu Thr Lys Lys Val Lys Gly Lys Ile Ile Thr Thr Pro Leu
            490                 495                 500

TTC TAT GAA ATA GGC AGA GCG ACA AGT GAG AAT ATT CCA GAA GAA GAG      1709
Phe Tyr Glu Ile Gly Arg Ala Thr Ser Glu Asn Ile Pro Glu Glu Glu
        505                 510                 515

GTT CTC AAG GGA GAG CTC GCT GGC ATA CTA TTG GCT GAA GGA ACG CTC      1757
Val Leu Lys Gly Glu Leu Ala Gly Ile Leu Leu Ala Glu Gly Thr Leu
    520                 525                 530

TTG AGG AAA GAC GTT GAA TAC TTT GAT TCA TCC CGC AAA AAA CGG AGG      1805
Leu Arg Lys Asp Val Glu Tyr Phe Asp Ser Ser Arg Lys Lys Arg Arg
535                 540                 545                 550

ATT TCA CAC CAG TAT CGT GTT GAG ATA ACC ATT GGG AAA GAC GAG GAG      1853
Ile Ser His Gln Tyr Arg Val Glu Ile Thr Ile Gly Lys Asp Glu Glu
                555                 560                 565

GAG TTT AGG GAT CGT ATC ACA TAC ATT TTT GAG CGT TTG TTT GGG ATT      1901
Glu Phe Arg Asp Arg Ile Thr Tyr Ile Phe Glu Arg Leu Phe Gly Ile
            570                 575                 580

ACT CCA AGC ATC TCG GAG AAG AAA GGA ACT AAC GCA GTA ACA CTC AAA      1949
Thr Pro Ser Ile Ser Glu Lys Lys Gly Thr Asn Ala Val Thr Leu Lys
        585                 590                 595

GTT GCG AAG AAG AAT GTT TAT CTT AAA GTC AAG GAA ATT ATG GAC AAC      1997
Val Ala Lys Lys Asn Val Tyr Leu Lys Val Lys Glu Ile Met Asp Asn
    600                 605                 610

ATA GAG TCC CTA CAT GCC CCC TCG GTT CTC AGG GGA TTC TTC GAA GGC      2045
Ile Glu Ser Leu His Ala Pro Ser Val Leu Arg Gly Phe Phe Glu Gly
615                 620                 625                 630

GAC GGT TCA GTA AAC AGG GTT AGG AGG AGT ATT GTT GCA ACC CAG GGT      2093
Asp Gly Ser Val Asn Arg Val Arg Arg Ser Ile Val Ala Thr Gln Gly
                635                 640                 645
```

-continued

```
ACA AAG AAC GAG TGG AAG ATT AAA CTG GTG TCA AAA CTG CTC TCC CAG     2141
Thr Lys Asn Glu Trp Lys Ile Lys Leu Val Ser Lys Leu Leu Ser Gln
            650                 655                 660

CTT GGT ATC CCT CAT CAA ACG TAC ACG TAT CAG TAT CAG GAA AAT GGG     2189
Leu Gly Ile Pro His Gln Thr Tyr Thr Tyr Gln Tyr Gln Glu Asn Gly
        665                 670                 675

AAA GAT CGG AGC AGG TAT ATA CTG GAG ATA ACT GGA AAG GAC GGA TTG     2237
Lys Asp Arg Ser Arg Tyr Ile Leu Glu Ile Thr Gly Lys Asp Gly Leu
    680                 685                 690

ATA CTG TTC CAA ACA CTC ATT GGA TTC ATC AGT GAA AGA AAG AAC GCT     2285
Ile Leu Phe Gln Thr Leu Ile Gly Phe Ile Ser Glu Arg Lys Asn Ala
695                 700                 705                 710

CTG CTT AAT AAG GCA ATA TCT CAG AGG GAA ATG AAC AAC TTG GAA AAC     2333
Leu Leu Asn Lys Ala Ile Ser Gln Arg Glu Met Asn Asn Leu Glu Asn
                715                 720                 725

AAT GGA TTT TAC AGG CTC AGT GAA TTC AAT GTC AGC ACG GAA TAC TAT     2381
Asn Gly Phe Tyr Arg Leu Ser Glu Phe Asn Val Ser Thr Glu Tyr Tyr
            730                 735                 740

GAG GGC AAG GTC TAT GAC TTA ACT CTT GAA GGA ACT CCC TAC TAC TTT     2429
Glu Gly Lys Val Tyr Asp Leu Thr Leu Glu Gly Thr Pro Tyr Tyr Phe
        745                 750                 755

GCC AAT GGC ATA TTG ACC CAT AAC TCC CTG TAC CCC TCA ATC ATC ATC     2477
Ala Asn Gly Ile Leu Thr His Asn Ser Leu Tyr Pro Ser Ile Ile Ile
    760                 765                 770

ACC CAC AAC GTC TCG CCG GAT ACG CTC AAC AGA GAA GGA TGC AAG GAA     2525
Thr His Asn Val Ser Pro Asp Thr Leu Asn Arg Glu Gly Cys Lys Glu
775                 780                 785                 790

TAT GAC GTT GCC CCA CAG GTC GGC CAC CGC TTC TGC AAG GAC TTC CCA     2573
Tyr Asp Val Ala Pro Gln Val Gly His Arg Phe Cys Lys Asp Phe Pro
                795                 800                 805

GGA TTT ATC CCG AGC CTG CTT GGA GAC CTC CTA GAG GAG AGG CAG AAG     2621
Gly Phe Ile Pro Ser Leu Leu Gly Asp Leu Leu Glu Glu Arg Gln Lys
            810                 815                 820

ATA AAG AAG AAG ATG AAG GCC ACG ATT GAC CCG ATC GAG AGG AAG CTC     2669
Ile Lys Lys Lys Met Lys Ala Thr Ile Asp Pro Ile Glu Arg Lys Leu
        825                 830                 835

CTC GAT TAC AGG CAG AGG GCC ATC AAG ATC CTG GCA AAC AGC ATC CTA     2717
Leu Asp Tyr Arg Gln Arg Ala Ile Lys Ile Leu Ala Asn Ser Ile Leu
    840                 845                 850

CCC GAG GAA TGG CTT CCA GTC CTC GAG GAA GGG GAG GTT CAC TTC GTC     2765
Pro Glu Glu Trp Leu Pro Val Leu Glu Glu Gly Glu Val His Phe Val
855                 860                 865                 870

AGG ATT GGA GAG CTC ATA GAC CGG ATG ATG GAG GAA AAT GCT GGG AAA     2813
Arg Ile Gly Glu Leu Ile Asp Arg Met Met Glu Glu Asn Ala Gly Lys
                875                 880                 885

GTA AAG AGA GAG GGC GAG ACG GAA GTG CTT GAG GTC AGT GGG CTT GAA     2861
Val Lys Arg Glu Gly Glu Thr Glu Val Leu Glu Val Ser Gly Leu Glu
            890                 895                 900

GTC CCG TCC TTT AAC AGG AGA ACT AAC AAG GCC GAG CTC AAG AGA GTA     2909
Val Pro Ser Phe Asn Arg Arg Thr Asn Lys Ala Glu Leu Lys Arg Val
        905                 910                 915

AAG GCC CTG ATT AGG CAC GAT TAT TCT GGC AAG GTC TAC ACC ATC AGA     2957
Lys Ala Leu Ile Arg His Asp Tyr Ser Gly Lys Val Tyr Thr Ile Arg
    920                 925                 930

CTG AAG TCG GGG AGG AGA ATA AAG ATA ACC TCT GGC CAC AGC CTC TTC     3005
Leu Lys Ser Gly Arg Arg Ile Lys Ile Thr Ser Gly His Ser Leu Phe
935                 940                 945                 950

TCT GTG AGA AAC GGG GAG CTC GTT GAA GTT ACG GGC GAT GAA CTA AAT     3053
Ser Val Arg Asn Gly Glu Leu Val Glu Val Thr Gly Asp Glu Leu Lys
                955                 960                 965
```

-continued

```
CCA GGT GAC CTC GTT GCA GTC CCG CGG AGA TTG GAG CTT CCT GAG AGA     3101
Pro Gly Asp Leu Val Ala Val Pro Arg Arg Leu Glu Leu Pro Glu Arg
            970                 975                 980

AAC CAC GTG CTG AAC CTC GTT GAA CTG CTC CTT GGA ACG CCA GAA GAA     3149
Asn His Val Leu Asn Leu Val Glu Leu Leu Leu Gly Thr Pro Glu Glu
        985                 990                 995

GAA ACT TTG GAC ATC GTC ATG ACG ATC CCA GTC AAG GGT AAG AAG AAC     3197
Glu Thr Leu Asp Ile Val Met Thr Ile Pro Val Lys Gly Lys Lys Asn
    1000                1005                1010

TTC TTT AAA GGG ATG CTC AGG ACT TTG CGC TGG ATT TTC GGA GAG GAA     3245
Phe Phe Lys Gly Met Leu Arg Thr Leu Arg Trp Ile Phe Gly Glu Glu
1015                1020                1025                1030

AAG AGG CCC AGA ACC GCG AGA CGC TAT CTC AGG CAC CTT GAG GAT CTG     3293
Lys Arg Pro Arg Thr Ala Arg Arg Tyr Leu Arg His Leu Glu Asp Leu
                1035                1040                1045

GGC TAT GTC CGG CTT AAG AAG ATC GGC TAC GAA GTC CTC GAC TGG GAC     3341
Gly Tyr Val Arg Leu Lys Lys Ile Gly Tyr Glu Val Leu Asp Trp Asp
            1050                1055                1060

TCA CTT AAG AAC TAC AGA AGG CTC TAC GAG GCG CTT GTC GAG AAC GTC     3389
Ser Leu Lys Asn Tyr Arg Arg Leu Tyr Glu Ala Leu Val Glu Asn Val
        1065                1070                1075

AGA TAC AAC GGC AAC AAG AGG GAG TAC CTC GTT GAA TTC AAT TCC ATC     3437
Arg Tyr Asn Gly Asn Lys Arg Glu Tyr Leu Val Glu Phe Asn Ser Ile
    1080                1085                1090

CGG GAT GCA GTT GGC ATA ATG CCC CTA AAA GAG CTG AAG GAG TGG AAG     3485
Arg Asp Ala Val Gly Ile Met Pro Leu Lys Glu Leu Lys Glu Trp Lys
1095                1100                1105                1110

ATC GGC ACG CTG AAC GGC TTC AGA ATG AGA AAG CTC ATT GAA GTG GAC     3533
Ile Gly Thr Leu Asn Gly Phe Arg Met Arg Lys Leu Ile Glu Val Asp
                1115                1120                1125

GAG TCG TTA GCA AAG CTC CTC GGC TAC TAC GTG AGC GAG GGC TAT GCA     3581
Glu Ser Leu Ala Lys Leu Leu Gly Tyr Tyr Val Ser Glu Gly Tyr Ala
            1130                1135                1140

AGA AAG CAG AGG AAT CCC AAA AAC GGC TGG AGC TAC AGC GTG AAG CTC     3629
Arg Lys Gln Arg Asn Pro Lys Asn Gly Trp Ser Tyr Ser Val Lys Leu
        1145                1150                1155

TAC AAC GAA GAC CCT GAA GTG CTG GAC GAT ATG GAG AGA CTC GCC AGC     3677
Tyr Asn Glu Asp Pro Glu Val Leu Asp Asp Met Glu Arg Leu Ala Ser
    1160                1165                1170

AGG TTT TTC GGG AAG GTG AGG CGG GGC AGG AAC TAC GTT GAG ATA CCG     3725
Arg Phe Phe Gly Lys Val Arg Arg Gly Arg Asn Tyr Val Glu Ile Pro
1175                1180                1185                1190

AAG AAG ATC GGC TAC CTG CTC TTT GAG AAC ATG TGC GGT GTC CTA GCG     3773
Lys Lys Ile Gly Tyr Leu Leu Phe Glu Asn Met Cys Gly Val Leu Ala
                1195                1200                1205

GAG AAC AAG AGG ATT CCC GAG TTC GTC TTC ACG TCC CCG AAA GGG GTT     3821
Glu Asn Lys Arg Ile Pro Glu Phe Val Phe Thr Ser Pro Lys Gly Val
            1210                1215                1220

CGG CTG GCC TTC CTT GAG GGG TAC TCA TCG GCG ATG GCG ACG TCC ACC     3869
Arg Leu Ala Phe Leu Glu Gly Tyr Ser Ser Ala Met Ala Thr Ser Thr
        1225                1230                1235

GAA CAA GAG ACT CAG GCT CTC AAC GAA AAG CGA GCT TTA GCG AAC CAG     3917
Glu Gln Glu Thr Gln Ala Leu Asn Glu Lys Arg Ala Leu Ala Asn Gln
    1240                1245                1250

CTC GTC CTC CTC TTG AAC TCG GTG GGG GTC TCT GCT GTA AAA CTT GGG     3965
Leu Val Leu Leu Leu Asn Ser Val Gly Val Ser Ala Val Lys Leu Gly
1255                1260                1265                1270

CAC GAC AGC GGC GTT TAC AGG GTC TAT ATA AAC GAG GAG CTC CCG TTC     4013
His Asp Ser Gly Val Tyr Arg Val Tyr Ile Asn Glu Glu Leu Pro Phe
```

-continued

```
            1275                1280                1285

GTA AAG CTG GAC AAG AAA AAG AAC GCC TAC TAC TCA CAC GTG ATC CCC     4061
Val Lys Leu Asp Lys Lys Lys Asn Ala Tyr Tyr Ser His Val Ile Pro
            1290                1295                1300

AAG GAA GTC CTG AGC GAG GTC TTT GGG AAG GTT TTC CAG AAA AAC GTC     4109
Lys Glu Val Leu Ser Glu Val Phe Gly Lys Val Phe Gln Lys Asn Val
        1305                1310                1315

AGT CCT CAG ACC TTC AGG AAG ATG GTC GAG GAC GGA AGA CTC GAT CCC     4157
Ser Pro Gln Thr Phe Arg Lys Met Val Glu Asp Gly Arg Leu Asp Pro
    1320                1325                1330

GAA AAG GCC CAG AGG CTC TCC TGG CTC ATT GAG GGG GAC GTA GTG CTC     4205
Glu Lys Ala Gln Arg Leu Ser Trp Leu Ile Glu Gly Asp Val Val Leu
1335                1340                1345                1350

GAC CGC GTT GAG TCC GTT GAT GTG GAA GAC TAC GAT GGT TAT GTC TAT     4253
Asp Arg Val Glu Ser Val Asp Val Glu Asp Tyr Asp Gly Tyr Val Tyr
                1355                1360                1365

GAC CTG AGC GTC GAG GAC AAC GAG AAC TTC CTC GTT GGC TTT GGG TTG     4301
Asp Leu Ser Val Glu Asp Asn Glu Asn Phe Leu Val Gly Phe Gly Leu
            1370                1375                1380

GTC TAT GCT CAC AAC AGC TAC TAC GGT TAC TAC GGC TAT GCA AGG GCG     4349
Val Tyr Ala His Asn Ser Tyr Tyr Gly Tyr Tyr Gly Tyr Ala Arg Ala
        1385                1390                1395

CGC TGG TAC TGC AAG GAG TGT GCA GAG AGC GTA ACG GCC TGG GGA AGG     4397
Arg Trp Tyr Cys Lys Glu Cys Ala Glu Ser Val Thr Ala Trp Gly Arg
    1400                1405                1410

GAG TAC ATA ACG ATG ACC ATC AAG GAG ATA GAG GAA AAG TAC GGC TTT     4445
Glu Tyr Ile Thr Met Thr Ile Lys Glu Ile Glu Glu Lys Tyr Gly Phe
1415                1420                1425                1430

AAG GTA ATC TAC AGC GAC ACC GAC GGA TTT TTT GCC ACA ATA CCT GGA     4493
Lys Val Ile Tyr Ser Asp Thr Asp Gly Phe Phe Ala Thr Ile Pro Gly
                1435                1440                1445

GCC GAT GCT GAA ACC GTC AAA AAG AAG GCT ATG GAG TTC CTC AAC TAT     4541
Ala Asp Ala Glu Thr Val Lys Lys Lys Ala Met Glu Phe Leu Asn Tyr
            1450                1455                1460

ATC AAC GCC AAA CTT CCG GGC GCG CTT GAG CTC GAG TAC GAG GGC TTC     4589
Ile Asn Ala Lys Leu Pro Gly Ala Leu Glu Leu Glu Tyr Glu Gly Phe
        1465                1470                1475

TAC AAA CGC GGC TTC TTC GTC ACG AAG AAG AAG TAT GCG GTG ATA GAC     4637
Tyr Lys Arg Gly Phe Phe Val Thr Lys Lys Lys Tyr Ala Val Ile Asp
    1480                1485                1490

GAG GAA GGC AAG ATA ACA ACG CGC GGA CTT GAG ATT GTG AGG CGT GAC     4685
Glu Glu Gly Lys Ile Thr Thr Arg Gly Leu Glu Ile Val Arg Arg Asp
1495                1500                1505                1510

TGG AGC GAG ATA GCG AAA GAG ACG CAG GCG AGG GTT CTT GAA GCT TTG     4733
Trp Ser Glu Ile Ala Lys Glu Thr Gln Ala Arg Val Leu Glu Ala Leu
                1515                1520                1525

CTA AAG GAC GGT GAC GTC GAG AAG GCC GTG AGG ATA GTC AAA GAA GTT     4781
Leu Lys Asp Gly Asp Val Glu Lys Ala Val Arg Ile Val Lys Glu Val
            1530                1535                1540

ACC GAA AAG CTG AGC AAG TAC GAG GTT CCG CCG GAG AAG CTG GTG ATC     4829
Thr Glu Lys Leu Ser Lys Tyr Glu Val Pro Pro Glu Lys Leu Val Ile
        1545                1550                1555

CAC GAG CAG ATA ACG AGG GAT TTA AAG GAC TAC AAG GCA ACC GGT CCC     4877
His Glu Gln Ile Thr Arg Asp Leu Lys Asp Tyr Lys Ala Thr Gly Pro
    1560                1565                1570

CAC GTT GCC GTT GCC AAG AGG TTG GCC GCG AGA GGA GTC AAA ATA CGC     4925
His Val Ala Val Ala Lys Arg Leu Ala Ala Arg Gly Val Lys Ile Arg
1575                1580                1585                1590

CCT GGA ACG GTG ATA AGC TAC ATC GTG CTC AAG GGC TCT GGG AGG ATA     4973
```

-continued

```
Pro Gly Thr Val Ile Ser Tyr Ile Val Leu Lys Gly Ser Gly Arg Ile
                1595                1600                1605

GGC GAC AGG GCG ATA CCG TTC GAC GAG TTC GAC CCG ACG AAG CAC AAG     5021
Gly Asp Arg Ala Ile Pro Phe Asp Glu Phe Asp Pro Thr Lys His Lys
            1610                1615                1620

TAC GAC GCC GAG TAC TAC ATT GAG AAC CAG GTT CTC CCA GCC GTT GAG     5069
Tyr Asp Ala Glu Tyr Tyr Ile Glu Asn Gln Val Leu Pro Ala Val Glu
        1625                1630                1635

AGA ATT CTG AGA GCC TTC GGT TAC CGC AAG GAA GAC CTG CGC TAC CAG     5117
Arg Ile Leu Arg Ala Phe Gly Tyr Arg Lys Glu Asp Leu Arg Tyr Gln
    1640                1645                1650

AAG ACG AGA CAG GTT GGT TTG AGT GCT TGG CTG AAG CCG AAG GGA ACT     5165
Lys Thr Arg Gln Val Gly Leu Ser Ala Trp Leu Lys Pro Lys Gly Thr
1655                1660                1665                1670

TGACCTTTCC ATTTGTTTTC CAGCGGATAA CCCTTTAACT TCCCTTTCAA AAACTCCCTT   5225

TAGGGAAAGA CCATGAAGAT AGAAATCCGG CGGCGCCCGG TTAAATACGC TAGGATAGAA   5285

GTGAAGCCAG ACGGCAGGGT AGTCGTCACT GCCCCGAGGG TTCAACGTTG AGAAGTT      5342
```

(2) INFORMATION FOR SEQ ID NO: 6:

(i) SEQUENCE CHARACTERISTICS:
(A) LENGTH: 5339 base pairs
(B) TYPE: nucleic acid
(C) STRANDEDNESS: double
(D) TOPOLOGY: linear (ii) MOLECULE TYPE: cDNA (vi) ORIGINAL SOURCE: Hyperthermophilic archaeon (xi) SEQUENCE DESCRIPTION: SEQ ID NO: 6:

```
GCTTGAGGGC CTGCGGTTAT GGGACGTTGC AGTTTGCGCC TACTCAAAGA TGCCGGTTTT     60

ATAACGGAGA AAAATGGGGA GCTATTACGA TCTCTCCTTG ATGTGGGGTT TACAATAAAG    120

CCTGGATTGT TCTACAAGAT TATGGGGGAT GAAAGATGAT CCTCGACACT GACTACATAA    180

CCGAGGATGG AAAGCCTGTC ATAAGAATTT TCAAGAAGGA AAACGGCGAG TTTAAGATTG    240

AGTACGACCG GACTTTTGAA CCCTACTTCT ACGCCCTCCT GAAGGACGAT TCTGCCATTG    300

AGGAAGTCAA GAAGATAACC GCCGAGAGGC ACGGGACGGT TGTAACGGTT AAGCGGGTTG    360

AAAAGGTTCA GAAGAAGTTC CTCGGGAGAC CAGTTGAGGT CTGGAAACTC TACTTTACTC    420

ATCCGCAGGA CGTCCCAGCG ATAAGGGACA AGATACGAGA GCATGGAGCA GTTATTGACA    480

TCTACGAGTA CGACATACCC TTCGCCAAGC GCTACCTCAT AGACAAGGGA TTAGTGCCAA    540

TGGAAGGCGA CGAGGAGCTG AAAATGCTCG CCTTCGACAT TCAAACTCTC TACCATGAGG    600

GCGAGGAGTT CGCCGAGGGG CCAATCCTTA TGATAAGCTA CGCCGACGAG GAAGGGGCCA    660

GGGTGATAAC TTGGAAGAAC GTGGATCTCC CCTACGTTGA CGTCGTCTCG ACGGAGAGGG    720

AGATGATAAA GCGCTTCCTC CGTGTTGTGA AGGAGAAAGA CCCGGACGTT CTCATAACCT    780

ACAACGGCGA CAACTTCGAC TTCGCCTATC TGAAAAAGCG CTGTGAAAAG CTCGGAATAA    840

ACTTCGCCCT CGGAAGGGAT GGAAGCGAGC CGAAGATTCA GAGGATGGGC GACAGGTTTG    900

CCGTCGAAGT GAAGGGACGG ATACACTTCG ATCTCTATCC TGTGATAAGA CGGACGATAA    960

ACCTGCCCAC ATACACGCTT GAGGCCGTTT ATGAAGCCGT CTTCGGTCAG CCGAAGGAGA   1020

AGGTTTACGC TGAGGAAATA ACACCAGCCT GGGAAACCGG CGAGAACCTT GAGAGAGTCG   1080

CCCGCTACTC GATGGAAGAT GCGAAGGTCA CATACGAGCT TGGGAAGGAG TTCCTTCCGA   1140

TGGAGGCCCA GCTTTCTCGC TTAATCGGCC AGTCCCTCTG GGACGTCTCC CGCTCCAGCA   1200
```

-continued

```
CTGGCAACCT CGTTGAGTGG TTCCTCCTCA GGAAGGCCCT ATGAGAGGAA TGAGCTGGCC   1260
CCGAACAAGC CCGATGAAAA GGAGCTGGCC AGAAGACGGC AGAGCTATGA AGGAGGCTAT   1320
GTAAAAGAGC CCGAGAGAGG GTTGTGGGAG AACATAGTGT ACCTAGATTT TAGATGCCAT   1380
CCAGCCGATA CGAAGGTTGT CGTCAAGGGG AAGGGGATTA TAAACATCAG CGAGGTTCAG   1440
GAAGGTGACT ATGTCCTTGG GATTGACGGC TGGCAGAGAG TTAGAAAAGT ATGGGAATAC   1500
GACTACAAAG GGGAGCTTGT AAACATAAAC GGGTTAAAGT GTACGCCCAA TCATAAGCTT   1560
CCCGTTGTTA CAAAGAACGA ACGACAAACG AGAATAAGAG ACAGTCTTGC TAAGTCTTTC   1620
CTTACTAAAA AAGTTAAGGG CAAGATAATA ACCACTCCCC TTTTCTATGA AATAGGCAGA   1680
GCGACAAGTG AGAATATTCC AGAAGAAGAG GTTCTCAAGG GAGAGCTCGC TGGCATAGTA   1740
TTGGCTGAAG GAACGCTCTT GAGGAAAGAC GTTGAATACT TTGATTCATC CCGCAAAAAA   1800
CGGAGGATTT CACACCAGTA TCGTGTTGAG ATAACCATTG GGAAAGACGA GGAGGAGTTT   1860
AGGGATCGTA TCACATACAT TTTTGAGCGT TTGTTTGGGA TTACTCCAAG CATCTCGGAG   1920
AAGAAAGGAA CTAACGCAGT AACACTCAAA GTTGCGAAGA AGAATGTTTA TCTTAAAGTC   1980
AAGGAAATTA TGGACAACAT AGAGTCCCTA CATGCCCCCT CGGTTCTCAG GGGATTCTTC   2040
GAAGGCGACG GTTCAGTAAA CAGGTTAGGA GGAGTATTGT TGCAACCCAG GGTACAAAGA   2100
ACGAGTGGAA GATTAAACTG GTGTCAAAAC TGCTCTCCCA GCTTGGTATC CCTCATCAAA   2160
CGTACACGTA TCAGTATCAG GAAAATGGGA AAGATCGGAG CAGGTATATA CTGGAGATAA   2220
CTGGAAAGGA CGGATTGATA CTGTTCCAAA CACTCATTGG ATTCATCAGT GAAAGAAAGA   2280
ACGCTCTGCT TAATAAGGCA ATATCTCAGA GGGAAATGAA CAACTTGGAA AACAATGGAT   2340
TTTACAGGCT CAGTGAATTC AATGTCAGCA CGGAATACTA TGAGGGCAAG GTCTATGACT   2400
TAACTCTTGA AGGAACTCCC TACTTTGCCA ATGGCATATT GACCCATAAC TCCCTGTACC   2460
CCTCAATCAT CATCACCCAC AACGTCTCGC CGGATACGCT CAACAGAGAA GGATGCAAGG   2520
AATATGACGT TGCCCCACAG GTCGGCCACC GCTTCTGCAA GGACTTCCCA GGATTTATCC   2580
CGAGCCTGCT TGGAGACCTC CTAGAGGAGA GGCAGAAGAT AAAGAAGAAG ATGAAGGCCA   2640
CGATTGACCC GATCGAGAGG AAGCTCCTCG ATTACAGGCA GAGGGCCATC AAGATCCTGG   2700
CAAACAGCAT CCTACCCGAG GAATGGCTTC CAGTCCTCGA GGAAGGGGAG GTTCACTTCG   2760
TCAGGATTGG AGAGCTCATA GACCGGATGA TGGAGGAAAA TGCTGGGAAA GTAAAGAGAG   2820
AGGGCGAGAC GGAAGTGCTT GAGGTCAGTG GGCTTGAAGT CCCGTCCTTT AACAGGAGAA   2880
CTAACAAGGC CGAGCTCAAG AGAGTAAAGG CCCTGATTAG GCACGATTAT TCTGGCAAGG   2940
TCTACACCAT CAGACTGAAG TCGGGGAGGA GAATAAAGAT AACCTCTGGC CACAGCCTCT   3000
TCTCTGTGAG AAACGGGGAG CTCGTTGAAG TTACGGGCGA TGAACTAAAG CCAGGTGACC   3060
TCGTTGCAGT CCCGCGGAGA TTGGAGCTTC CTGAGAGAAA CCACGTGCTG AACCTCGTTG   3120
AACTGCTCCT TGGAACGCCA GAAGAAGAAA CTTTGGACAT CGTCATGACG ATCCCAGTCA   3180
AGGGTAAGAA GAACTTCTTT AAAGGGATGC TCAGGACTTT GCGCTGGATT TTCGGAGAGG   3240
AAAAGAGGCC CAGAACCGCG AGACGCTATC TCAGGCACCT TGAGGATCTG GGCTATGTCC   3300
GGCTTAAGAA GATCGGCTAC GAAGTCCTCG ACTGGGACTC ACTTAAGAAC TACAGAAGGC   3360
TCTACGAGGC GCTTGTCGAG AACGTCAGAT ACAACGGCAA CAAGAGGGAG TACCTCGTTG   3420
AATTCAATTC CATCCGGGAT GCAGTTGGCA TAATGCCCCT AAAAGAGCTG AAGGAGTGGA   3480
AGATCGGCAC GCTGAACGGC TTCAGAATGA GAAAGCTCAT TGAAGTGGAC GAGTCGTTAG   3540
```

-continued

```
CAAAGCTCCT CGGCTACTAC GTGAGCGAGG GCTATGCAAG AAAGCAGAGG AATCCCAAAA   3600

ACGGCTGGAG CTACAGCGTG AAGCTCTACA ACGAAGACCC TGAAGTGCTG GACGATATGG   3660

AGAGACTCGC CAGCAGGTTT TTCGGGAAGG TGAGGCGGGG CAGGAACTAC GTTGAGATAC   3720

CGAAGAAGAT CGGCTACCTG CTCTTTGAGA ACATGTGCGG TGTCCTAGCG GAGAACAAGA   3780

GGATTCCCGA TGGCGTCTTC ACGTCCCCGA AAGGGGTTCG GCTGGCCTTC CTTGAGGGGT   3840

ACTCATCGGC GATGGCGACG TCCACCGAAC AAGAGACTCA GGCTCTCAAC GAAAAGCGAG   3900

CTTTAGCGAA CCAGCTCGTC CTCCTCTTGA ACTCGGTGGG GGTCTCTGCT GTAAAACTTG   3960

GGCACGACAG CGGCGTTTAC AGGGTCTATA TAAACGAGGA GCTCCCGTTC GTAAAGCTGG   4020

ACAAGAAAAA GAACGCCTAC TACTCACACG TGATCCCCAA GGAAGTCCTG AGCGAGGTCT   4080

TTGGGAAGGT TTTCCAGAAA AACGTCAGTC CTCAGACCTT CAGGAAGATG GTCGAGGACG   4140

GAAGACTCGA TCCCGAAAAG GCCCAGAGGC TCTCCTGGCT CATTGAGGGG GACGTAGTGC   4200

TCGACCGCGT TGAGTCCGTT GATGTGGAAG ACTACGATGG TTATGTCTAT GACCTGAGCG   4260

TCGAGGACAA CGAGAACTTC CTCGTTGGCT TTGGGTTGGT CTATGCTCAC AACAGCTACT   4320

ACGGTTACTA CGGCTATGCA AGGGCGCGCT GGTACTGCAA GGAGTGTGCA GAGAGCGTAA   4380

CGGCCTGGGG AAGGGAGTAC ATAACGATGA CCATCAAGGA GATAGAGGAA AAGTACGGCT   4440

TTAAGGTAAT CTACAGCGAC ACCGACGGAT TTTTTGCCAC AATACCTGGA GCCGATGCTG   4500

AAACCGTCAA AAAGAAGGCT ATGGAGTTCC TCAACTATAT CAACGCCAAA CTTCCGGGCG   4560

CGCTTGAGCT CGAGTACGAG GGCTTCTACA AACGCGGCTT CTTCGTCACG AAGAAGAAGT   4620

ATGCGGTGAT AGACGAGGAA GGCAAGATAA CAACGCGCGG ACTTGAGATT GTGAGGCGTG   4680

ACTGGAGCGA GATAGCGAAA GAGACGCAGG CGAGGGTTCT TGAAGCTTTG CTAAAGGACG   4740

GTGACGTCGA GAAGGCCGTG AGGATAGTCA AAGAAGTTAC CGAAAAGCTG AGCAAGTACG   4800

AGGTTCCGCC GGAGAAGCTG GTGATCCACG AGCAGATAAC GAGGGATTTA AAGGACTACA   4860

AGGCAACCGG TCCCCACGTT GCCGTTGCCA AGAGGTTGGC CGCGAGAGGA GTCAAAATAC   4920

GCCCTGGAAC GGTGATAAGC TACATCGTGC TCAAGGGCTC TGGGAGGATA GGCGACAGGG   4980

CGATACCGTT CGACGAGTTC GACCCGACGA AGCACAAGTA CGATGCCGAG TACTACATTG   5040

AGAACCAGGT TCTCCCAGCC GTTGAGAGAA TTCTGAGAGC CTTCGGTTAC CGCAAGGAAG   5100

ACCTGCGCTA CCAGAAGACG AGACAGGTTG GTTTGAGTGC TTGGCTGAAG CCGAAGGGAA   5160

CTTGACCTTT CCATTTGTTT TCCAGCGGAT AACCCTTTAA CTTCCCTTTC AAAAACTCCC   5220

TTTAGGGAAA GACCATGAAG ATAGAAATCC GGCGGCGCCC GGTTAAATAC GCTAGGATAG   5280

AAGTGAAGCC AGACGGCAGG GTAGTCGTCA CTGCCCCGAG GGTTCAACGT TGAGAAGTT    5339
```

(2) INFORMATION FOR SEQ ID NO: 7:

(i) SEQUENCE CHARACTERISTICS:
(A) LENGTH: 24 base pairs
(B) TYPE: nucleic acid
(C) STRANDEDNESS: double
(D) TOPOLOGY: linear (ii) MOLECULE TYPE: other nucleic acid (xi) SEQUENCE DESCRIPTION: SEQ ID NO: 7:

```
GGATTAGTGC CAATGGAAGG CGAC                                          24
```

(2) INFORMATION FOR SEQ ID NO: 8:

(i) SEQUENCE CHARACTERISTICS:

-continued (A) LENGTH: 24 base pairs
(B) TYPE: nucleic acid
(C) STRANDEDNESS: double
(D) TOPOLOGY: linear (ii) MOLECULE TYPE: other nucleic acid (xi) SEQUENCE DESCRIPTION: SEQ ID NO: 8:

GAGGGCGAAG TTTATTCCGA GCTT 24

(2) INFORMATION FOR SEQ ID NO: 9:

(i) SEQUENCE CHARACTERISTICS:
(A) LENGTH: 324 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO: 9:

GGATTAGTGC CAATGGAAGG CGACGAGGAG CTGAAAATGC TCGCCTTCGA CATTCAAACT 60

CTCTACCATG AGGGCGAGGA GTTCGCCGAG GGGCCAATCC TTATGATAAG CTACGCCGAC 120

GAGGAAGGGG CCAGGGTGAT AACTTGGAAG AACGTGGATC TCCCCTACGT TGACGTCGTC 180

TCGACGGAGA GGGAGATGAT AAAGCGCTTC CTCCGTGTTG TGAAGGAGAA AGACCCGGAC 240

GTTCTCATAA CCTACAACGG CGACAACTTC GACTTCGCCT ATCTGAAAAA GCGCTGTGAA 300

AAGCTCGGAA TAAACTTCGC CCTC 324

(2) INFORMATION FOR SEQ ID NO: 10:

(i) SEQUENCE CHARACTERISTICS:
(A) LENGTH: 108 amino acids
(B) TYPE: amino acid
(C) STRANDEDNESS: double
(D) TOPOLOGY: linear (ii) MOLECULE TYPE: protein (xi) SEQUENCE DESCRIPTION: SEQ ID NO: 10:

Gly Leu Val Pro Met Glu Gly Asp Glu Glu Leu Lys Met Leu Ala Phe
5 10 15

Asp Ile Gln Thr Leu Tyr His Glu Gly Glu Glu Phe Ala Glu Gly Pro
20 25 30

Ile Leu Met Ile Ser Tyr Ala Asp Glu Glu Gly Ala Arg Val Ile Thr
35 40 45

Trp Lys Asn Val Asp Leu Pro Tyr Val Asp Val Val Ser Thr Glu Arg
50 55 60

Glu Met Ile Lys Arg Phe Leu Arg Val Val Lys Glu Lys Asp Pro Asp
65 70 75 80

Val Leu Ile Thr Tyr Asn Gly Asp Asn Phe Asp Phe Ala Tyr Leu Lys
85 90 95

Lys Arg Cys Glu Lys Leu Gly Ile Asn Phe Ala Leu
100 105

(2) INFORMATION FOR SEQ ID NO: 11:

(i) SEQUENCE CHARACTERISTICS:
(A) LENGTH: 42 base pairs
(B) TYPE: nucleic acid
(C) STRANDEDNESS: single
(D) TOPOLOGY: linear -continued (ii) MOLECULE TYPE: other nucleic acid (xi) SEQUENCE DESCRIPTION: SEQ ID NO: 11:

GCCATCAAGA TCCTGGCAAA CAGCTACTAC GGTTACTACG GC 42

(2) INFORMATION FOR SEQ ID NO: 12:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 12:

GATGGATCCA ACTTCTCAAC GTTGAACCCT CG 32

(2) INFORMATION FOR SEQ ID NO: 13:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 13:

GAACATAGTG TACCTAGATT TTAGATCCCT GTACCCCTCA ATCATC 46

(2) INFORMATION FOR SEQ ID NO: 14:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 14:

GCCGTAGTAA CCGTAGTAGC TGTTTGCCAG GATCTTGATG GC 42

(2) INFORMATION FOR SEQ ID NO: 15:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO: 15:

ATCGATATCC TCGACACTGA CTACATAACC GAG 33

(2) INFORMATION FOR SEQ ID NO: 16:

(i) SEQUENCE CHARACTERISTICS:
(A) LENGTH: 46 base pairs
(B) TYPE: nucleic acid
(C) STRANDEDNESS: single
(D) TOPOLOGY: linear -continued (ii) MOLECULE TYPE: other nucleic acid (xi) SEQUENCE DESCRIPTION: SEQ ID NO: 16:

```
GATGATTGAG GGGTACAGGG ATCTAAAATC TAGGTACACT ATGTTC                    46
```